US011273015B2

(12) United States Patent
Chun et al.

(10) Patent No.: US 11,273,015 B2
(45) Date of Patent: Mar. 15, 2022

(54) FABRICATION AND INSTALLATION OF A DENTAL IMPLANT

(71) Applicant: Hankookin, Inc., Raleigh, NC (US)

(72) Inventors: James Jiwen Chun, Raleigh, NC (US); Angela Soyoung Chun, Raleigh, NC (US); Andrew Youngho Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 94 days.

(21) Appl. No.: 16/423,141

(22) Filed: May 27, 2019

(65) Prior Publication Data
US 2019/0274792 A1    Sep. 12, 2019

Related U.S. Application Data

(63) Continuation-in-part of application No. 12/878,039, filed on Sep. 9, 2010, now Pat. No. 10,299,895.

(51) Int. Cl.
*A61C 8/00*    (2006.01)

(52) U.S. Cl.
CPC .......... *A61C 8/0033* (2013.01); *A61C 8/0037* (2013.01); *A61C 8/0068* (2013.01); *A61C 8/0069* (2013.01); *A61C 2008/0046* (2013.01)

(58) Field of Classification Search
CPC ... A61C 8/0033; A61C 8/0037; A61C 8/0068; A61C 8/0069; A61C 8/0018; A61C 8/005; A61C 8/0048; A61C 8/00; A61C 2008/0046; A61C 8/0012
USPC ......... 433/172–175, 169, 177, 201.1; 606/73
See application file for complete search history.

(56) References Cited

U.S. PATENT DOCUMENTS

| | | | |
|---|---|---|---|
| 5,601,429 A * | 2/1997 | Blacklock | A61C 8/0022 433/172 |
| 5,890,902 A * | 4/1999 | Sapian | A61C 8/0048 433/173 |
| 7,361,369 B2 * | 4/2008 | Liebschner | A61C 8/00 424/426 |
| 9,572,639 B2 * | 2/2017 | Ten Bruggenkate | A61C 8/0022 |

(Continued)

FOREIGN PATENT DOCUMENTS

| | | | |
|---|---|---|---|
| CN | 1668256 A * | 9/2005 | A61L 27/56 |
| WO | WO-03045268 A1 * | 6/2003 | A61C 8/0015 |

OTHER PUBLICATIONS

Gahlert, Ceramic Dental Implant, WO-03045268,—machine translation of the specification (Year: 2001).*

*Primary Examiner* — Nicholas D Lucchesi
*Assistant Examiner* — Mirayda A Aponte
(74) *Attorney, Agent, or Firm* — Ashok Tankha

(57) ABSTRACT

A dental implant for supporting periodontal tissue and the supporting bone is provided. The dental implant includes an implant member with inner canal for insertion into a periodontal bone socket, and an anchoring assembly. The anchoring assembly includes a first fastening element and radially equidistant cylindrical members. The first fastening element engages the implant member within the hollow axial cavity. The root section includes through-holes for radially and forcibly sliding the cylindrical members through them. When the first fastening element apically advances within the hollow axial cavity, the cylindrical members generate an anchoring force to anchor the dental implant.

21 Claims, 23 Drawing Sheets

(56) References Cited

U.S. PATENT DOCUMENTS

2007/0162024 A1* 7/2007 Siemonsmeier ..... A61C 8/0018
606/312
2008/0090207 A1* 4/2008 Rubbert ............... A61C 8/0036
433/171

* cited by examiner

FABRICATION AND INSTALLATION OF A DENTAL IMPLANT

CROSS REFERENCE TO RELATED APPLICATIONS

This application is a continuation-in-part application of non-provisional patent application Ser. No. 12/878,039 titled "Fabrication And Installation Of A Dental Implant", filed in the United States Patent and Trademark Office on Sep. 9, 2010. The specification of the above referenced patent application is incorporated herein by reference in its entirety.

BACKGROUND

Dental implant therapy offers a method for restoring non-restorable teeth and edentulous dental sites in patients. Most dental implant systems hitherto require surgeries to drill precise pre-designed implant space such that an identically shaped prefabricated dental implant can be inserted into the implant space. Surgically preparing the implant space requires extensive diagnostic planning, invasive surgery, and an extended healing time. If the planned implant sites are close to the sinus or the nerve canal, the placement of the dental implant is unsuitable, and extensive bone graft surgery is generally required to build a suitable implant site before the dental implant can be inserted. Moreover, the invasive surgery may damage the periodontal and nerve tissue, and supporting bone, and may occasionally result in numbness of the tooth, potential loss of stability and retention of the dental implant.

Hence, there is a long felt but unresolved need for a method and system for fabricating and installing a dental implant that allows preservation of the supporting periodontal and nerve tissue and the supporting bone while maximizing retention and stability of the dental implant.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The method and system for a dental implant disclosed herein addresses the above stated need for fabricating and installing the dental implant that preserves periodontal and nerve tissue and the supporting bone in implant sites during installation and that maximizes the retention and stability of the installed dental implant. The method and system disclosed herein enables fabrication and non-invasive installation and restoration of the dental implant, preferably in one clinical appointment in a single patient visit, and thus also avoids extensive planning, invasive surgery, and long healing time.

The dental implant disclosed herein comprises an implant member for insertion into a periodontal bone socket of an extracted natural tooth, and an anchoring assembly. The implant member substantially resembles a natural tooth. The implant member comprises a coronal section and a root section. The root section of the implant member comprises a coronal end, a mid-portion, and a conical apical end. The coronal section axially extends from the coronal end of the root section. The implant member further comprises multiple hook shaped extensions circumferentially disposed around the root section of the implant member. The anchoring assembly is positioned within a hollow axial cavity of the implant member. The anchoring assembly anchors the implant member within the periodontal bone socket. The anchoring assembly comprises a first fastening element and one or more radial and equidistant cylindrical members. The first fastening element is engaged with the implant member and positioned within the hollow axial cavity. The first fastening element comprises an apical section having a conical shaft and a truncated end. The radial and equidistant cylindrical members of the anchoring assembly are positioned proximal to the root section of the implant member. The root section of the implant member comprises one or more through-holes for radially and forcibly sliding the cylindrical members through the through-holes. Each of the cylindrical members comprises a first end that interfaces with the conical shaft of the first fastening element, and a second end that interfaces substantially uniformly against a surface of the periodontal bone socket, for example, the surface of the surrounding bone socket, herein referred to as the "periodontal bone surface". The implant member further comprises a tapered inner canal extending from a base of the hollow axial cavity to the apical end of the root section. The tapered inner canal of the dental implant is further configured for allowing excess bone filler materials to escape from the surface of the periodontal bone socket through the tapered inner canal.

In an embodiment, the first fastening element is threaded to screwably engage the hollow axial cavity of the implant member. The first fastening element further comprises a coronal screw head and a screwable inner canal seal for tightening or releasing the first fastening element within the hollow axial cavity. The first fastening element apically advances within the hollow axial cavity when the first fastening element is tightened by turning the coronal screw head and the screwable inner canal seal. When the first fastening element is apically advanced within the hollow axial cavity of the implant member, the conical shaft of the first fastening element radially and outwardly pushes the cylindrical members through the through-holes, whereby the second end of each of the cylindrical members presses substantially uniformly against the periodontal bone surface to generate an anchoring force to anchor the implant member within the periodontal bone socket. After installation, the first fastening element thus enables a dentist to precisely control the anchoring force generated by the cylindrical members using the coronal screw head of the first fastening element.

The hook shaped extensions are fabricated to point upwards towards the coronal section of the implant member circumferentially disposed around on an outer surface of the root section of the implant member anchor the periodontal bone surface for impeding coronal movement of the inserted implant member within the periodontal bone socket. The outer surface of the implant member is a sandblasted micro-textured surface. The sandblasted micro-textured surface increases the surface area to allow sufficient bone growth. The outer surface of the implant member further comprises retentive grooves along a mid-portion of the root section of the implant member to increase contact area between the implant member and the periodontal bone surface resulting in denser bone formation. New bone tissue can be formed into the space between the retentive grooves to permanently secure the implant member inside the periodontal bone socket. In an embodiment, the implant member further comprises one or more longitudinal grooves parallel to the periodontal bone socket or one or more spiral grooves diagonal to the periodontal bone socket for allowing debris to escape out of the periodontal bone socket during the insertion of the implant member into the periodontal bone socket.

The dental implant disclosed herein further comprises a composite packing filled with tooth filling composite materials. The composite packing is disposed on a coronal surface of the coronal section of the implant member. The composite packing avoids direct occlusal contact of the implant member with the opposing teeth to reduce parafunctional interferences during an osseointegration period of the dental implant. The inserted dental implant is loaded with a permanent crown and/or a pre-fabricated tooth colored layer after the osseointegration period of the dental implant. In an embodiment, temporary crowns are placed during the healing period before the dental implant is bio-integrated with the supporting periodontal bone structure, and thereafter replaced by a permanent crown by either cementation or screws. In case of the temporary crowns, the biting surface is designed to avoid occlusal contact with the opposing teeth surface. An interstitial space is defined between the periodontal bone surface and the outer surface of the implant member after the insertion of the implant member into the periodontal bone socket. This interstitial space is filled, for example, with a bone filler material, an osteogenic material, and antibiotic agents to ensure bone regeneration and long term stability of the dental implant. The osteogenic material in the interstitial space and the retentive grooves induce bone into the retention grooves of the implant member and ensure long term stability and longevity of the dental implant.

The dental implant further comprises a second fastening element positioned within the tapered inner canal. The second fastening element comprises a screw head, a truncated end, and a coronal screw body. The second fastening element is configured to screwably engage the tapered inner canal of the implant member, wherein the second fastening element is tightened or released within the hollow axial cavity using the screw head. The second fastening element apically advances within the tapered inner canal when the second fastening element is tightened by turning the screw head.

In the method disclosed herein for providing the dental implant, one or more undercut area at a root of the natural tooth are determined that prevents insertion of the dental implant. The determined one or more undercut area is removed by filling the undercut area using one or more bone filler material thereby allowing insertion of the dental implant. In another embodiment, one or more insufficient bone area at the root of the natural tooth is determined before inserting the implant member into the periodontal bone socket. The dental implant is then modified to allow sufficient bone growth using one or more bone filler material if the root of the natural tooth does not have sufficient bone support. In the method for providing the dental implant, a traditional implant drill is used for drilling an additional implant space. An additional anchorage is provided in the implant member using the traditional implant drill within the periodontal bone socket of the dental implant.

In the method and system disclosed herein for fabricating the dental implant, high resolution three dimensional (3D) images of a natural tooth and a corresponding periodontal bone socket of the natural tooth are captured, for example, before the extraction of the natural tooth. These three dimensional images of the periodontal bone socket are used to digitally simulate the insertion of the dental implant into the periodontal bone socket to establish a path for inserting the dental implant. The dental implant is fabricated and milled according to a treatment plan based on the digital simulation using a fabricator. The fabricator comprises a computer aided design and computer aided manufacturing (CAD/CAM) milling machine and a customized surgical guide. The captured high-resolution three-dimensional images of the natural tooth are used for designing and milling the dental implant by the computer aided design and computer aided manufacturing (CAD/CAM) milling machine. The customized surgical guide acts as an anchor to extrude the natural tooth from the periodontal bone socket, guides precise insertion and tapping of the dental implant into the periodontal bone socket along the exact path of the extracted natural tooth, and acts as a protection shield from infection in the oral cavity during the insertion process of the dental implant. The additional anchorage via the traditional implant drill is incorporated in the three-dimensional planning of the implant member, and the drill space is prepared using the customized surgical guide. The fabricated dental implant is inserted into the periodontal bone socket based on the established path for insertion and the treatment plan. A coronal surface of the coronal section of the implant member of the inserted dental implant is filled with tooth filling composite materials for the osseointegration period of the dental implant. The inserted dental implant is loaded with a permanent crown and/or one or more pre-fabricated tooth colored layers at the end of the osseointegration period of the dental implant.

The dental implant is designed to maintain a distance of at least a thousand microns between the dental implant and one or more of an adjacent nerve canal, an adjacent sinus, and an adjacent blood vessel by the computer aided design and computer aided manufacturing (CAD/CAM) milling machine. Furthermore, the dental implant is designed to maintain an interstitial space of at least thirty microns between a coronal end and an apical end of a root section of the dental implant and the periodontal bone socket, an interstitial space of at least ninety microns between a midportion of the root section of the dental implant and the periodontal bone socket by the computer aided design and computer aided manufacturing (CAD/CAM) milling machine. The computer aided design and computer aided manufacturing (CAD/CAM) milling machine is further configured for creating one or more concentric retentive grooves along an outer surface of a mid-portion of the root section of the implant member, wherein adjacent grooves define ridges formed there between. An anchoring force required for anchoring the designed dental implant within the periodontal bone socket is predetermined by the digital simulator.

The dental implant is designed using the high resolution three-dimensional (3D) images of the original shape of the tooth to be extracted and the periodontal bone socket with resolutions of close to 30 μm/pixel. The extraction process weakens and widens the periodontal socket space in the less dense area and also in the area that bears stronger extraction force. These variations of the three-dimensional shape of the periodontal socket space are incorporated into the three-dimensional planning of the implant member. The height of the hook shaped extensions also varies with the bone density. If the bone density is low, the implant member with higher hook shaped extensions is inserted into the periodontal bone socket and provides strong retention with the supporting bone structure. This eliminates the need for traumatic surgery to prepare the implant space. The selection of the implant site and the path for insertion of the dental implant are based on the high-resolution 3D images of the periodontal bone socket and the simulation of the insertion of the dental implant into the periodontal bone socket.

Human errors in pre-surgical site selection are eliminated, because the odds of encountering a nerve, sinus or a major blood vessel in the socket of the tooth are excluded. The digital simulation also eliminates errors in implant design, site selection, and injury to nerves or blood vessels. If the implant member of the dental implant disclosed herein is positioned from 1000 µm to 2000 µm from the nerve canal, a separation space is planned to place the bone filler materials to maintain a distance of from 1000 µm to 2000 µm between the implant member and the nerve canal. The method and system disclosed herein enables direct placement of implants at implant sites heretofore determined to be unsuited for implants due to insufficient bone thickness such as the upper molar near the sinus floor, etc. The method and system disclosed herein enables the insertion of the dental implant without requiring any bone graft or sinus lift procedures. These and other advantages lead to a dramatic reduction of patient discomfort and clinical cost of the implant procedure. Furthermore, at the completion of the implant procedure according to the method and system disclosed herein, the periodontal bone socket is surrounded by a thicker cortical bone which provides stronger bone support for the dental implant, as opposed to the spongy bone structure supporting traditional implants.

The captured high-resolution three-dimensional images of the natural tooth is further enhanced using a two-dimensional periapical X-ray image by overlapping the captured high-resolution three-dimensional images with the two-dimensional periapical X-ray image of the natural tooth. The two-dimensional periapical X-ray image is further configured for converting a density function of the captured one or more three dimensional images to a density function of the two-dimensional periapical X-ray images thereby improving the resolution of the captured three-dimensional images of the natural tooth.

In an embodiment, a tooth extractor is used for extracting the natural tooth. The tooth extractor comprises a one or more facial and lingual bracing parts, a lift button, and a vibrational force transducer. The facial and lingual bracing parts are positioned on the natural tooth to be extracted thereby holding firmly the coronal portion of the natural tooth with a metal ring and tightened using a tightening screw. The lift button is positioned on top of the metal ring connecting to a lever for providing a strong lifting force in a direction coronal to extract the natural tooth along the path of eruption determined by one or more three dimensional images of the root of the natural tooth. The vibrational force transducer is positioned on top of the lift button thereby loosening the periodontal ligament before the extraction of the natural tooth.

The dental implant is inserted into the periodontal bone socket of the extracted tooth immediately after the atraumatic extraction of the tooth via the vibrational force transducer to tap the implant member into the periodontal bone socket through precision guided incremental steps. In an embodiment, the coronal section of the implant member of the dental implant is restored immediately following the implant procedure, for example, at the same appointment without the need to wait for soft tissue healing. The method and system disclosed herein enables placement of the dental implant into a multi-rooted tooth socket. The unfilled undercut spaces are filled with the proper amount of bone filler material. The dental implant and the method and system disclosed herein for installing and restoring the dental implant can be standardized to reduce the clinical cost of implant therapies. With onsite 3D X-ray imaging, computer aided design (CAD)/computer aided manufacturing (CAM) milling machines, and a pre-machined implant block for the implant member, the diagnosis, treatment planning, implant and restoration fabrication, atraumatic extraction, implant placement and preliminary restoration is accomplished in a single clinical appointment.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIGS. 1C exemplarily illustrates an enlarged view of a hook shaped micro-extension disposed on a root section of an implant member of the dental implant. FIG. 1D exemplarily illustrates an enlarged view of another hook shaped micro-extension disposed on the root section of the implant member of the dental implant.

FIG. 11A exemplarily illustrates an exploded front view of the dental implant with a tapered inner canal.

FIG. 11B exemplarily illustrates an enlarged view of the inner canal seal.

DETAILED DESCRIPTION OF THE INVENTION

Figure 1A:
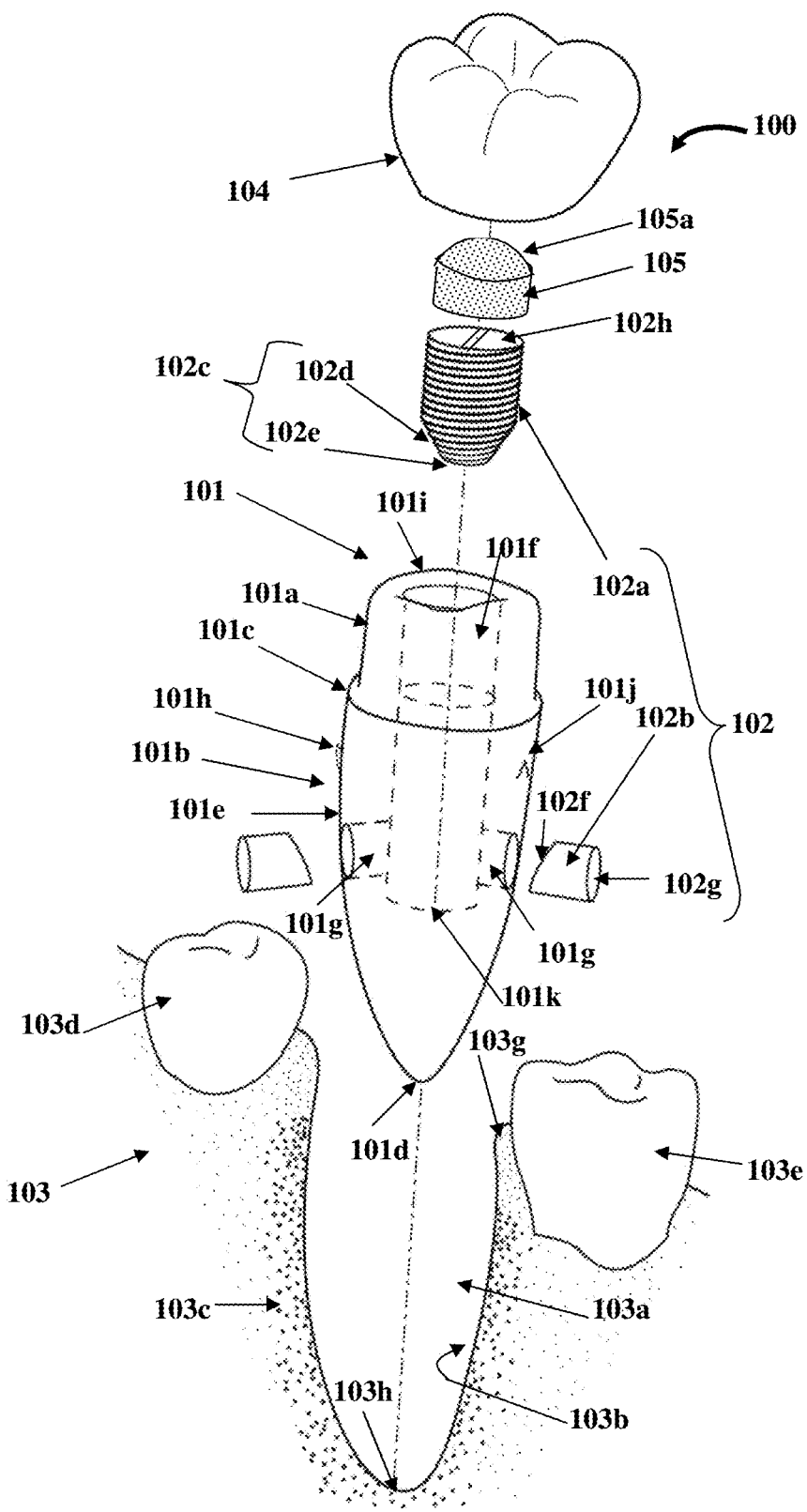
FIG. 1A illustrates an exploded perspective view of a dental implant for a patient.

FIG. 1A illustrates an exploded perspective of a dental implant 100 for a patient. The dental implant 100 comprises an implant member 101, substantially resembling a natural tooth, for insertion into a periodontal bone socket 103a of an extracted natural tooth. The extracted tooth, for example, lies adjacent to natural teeth 103d and 103e. As used herein, the term "periodontal bone socket" or "periodontal socket" refers to the socket(s) of the tooth/teeth 103d and 103e, also referred to as the dental alveolus in the maxillary and mandibular bones 103, surrounded by supporting bone and tissues of the periodontium or periodontal bone structure 103c. The implant member 101 comprises a coronal section 101a and a root section 101b. The root section 101b of the implant member 101 comprises a coronal end 101c, a mid-portion 101e, and a conical apical end 101d. The coronal section 101a axially extends from the coronal end 101c of the root section 101b. As used herein, the "coronal end" refers to an end 101c of the root section 101b of the implant member 101 or an end section of any other component that is disposed in the direction towards the crown 104 of a tooth 103d or 103e. As used herein, the "apical end" refers to an end 101d of the root section 101b of the implant member 101 or an end section of any other component that is disposed in the direction towards the root tip 101d of a tooth 103d or 103e.

The dental implant 100 disclosed herein further comprises an anchoring assembly 102 positioned within a hollow axial cavity 101f of the implant member 101. The anchoring assembly 102 anchors the implant member 101 within the periodontal bone socket 103a. The anchoring assembly 102 comprises a first fastening element 102a that engages the implant member 101 from within the hollow axial cavity 101f of the implant member 101. The first fastening element 102a comprises a coronal screw head 102h and an apical section 102c having a conical shaft 102d and a truncated end 102e. The coronal screw head 102h is used for tightening or releasing the first fastening element 102a within the hollow axial cavity 101f of the implant member 101. The coronal screw head 102h can be accessed from the coronal section 101a of the implant member 101.

The anchoring assembly 102 further comprises one or more radial and equidistant cylindrical members 102b positioned near the root section 101b of the implant member 101, for example, on the mid-portion 101e of the root section 101b of the implant member 101. The root section 101b of the implant member 101 comprises one or more through-holes 101g for radially and forcibly sliding the cylindrical members 102b through the through-holes 101g. The hollow axial cavity 101f of the implant member 101 is in fluid communication with each of the through-holes 101g in the root section 101b of the implant member 101. Each of the cylindrical members 102b comprises a first end 102f that contacts and interfaces with the conical shaft 102d of the first fastening element 102a, and a second end 102g that contacts and interfaces substantially uniformly against a surface 103b of the periodontal bone socket 103a, herein referred to as the "periodontal bone surface". The first end 102f of each of the cylindrical members 102b is concaved and beveled to make a flush contact with the conical shaft 102d of the first fastening element 102a. A temporary crown 104 and/or a composite packing 105 is placed over a coronal surface 101i of the coronal section 101a of the implant member 101 to reduce para-functional interferences during an osseointegration period of the dental implant 100. The implant member 101 further comprises a tapered inner canal 1101. The position and structure of the tapered inner canal 1101 is exemplarily illustrated in the detailed description of FIG. 11A. The dental implant 100 further comprises a second fastening element 1102. The structure and position of the second fastening element 1102 is exemplarily illustrated in the detailed description of FIG. 11A.

Figure 1B:
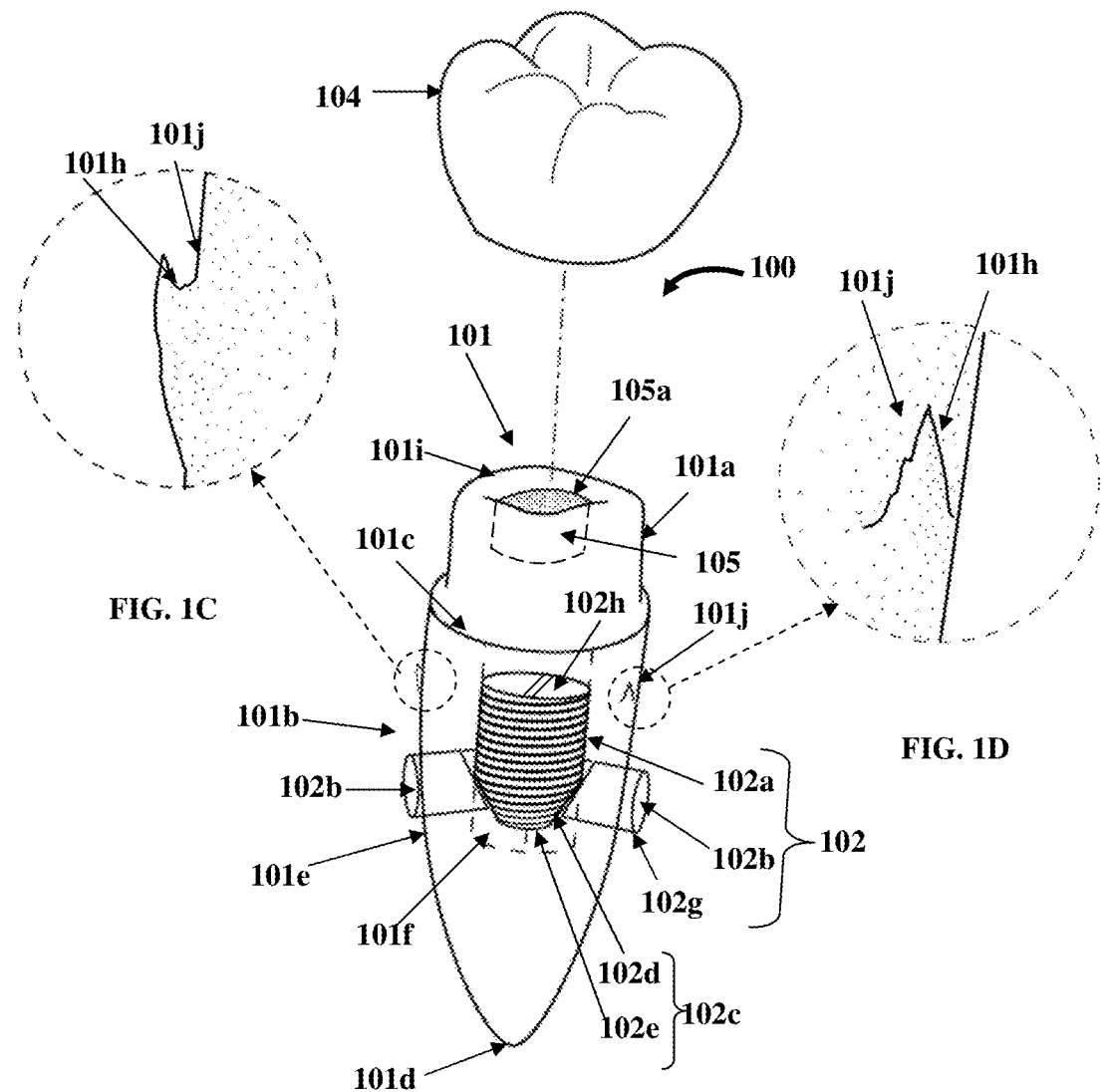
FIG. 1B exemplarily illustrates a perspective view of the dental implant.

FIG. 1B exemplarily illustrates a perspective view of the dental implant 100. As illustrated in FIGS. 1A-1B, the implant member 101 further comprises multiple hook shaped micro-extensions 101h fabricated to point upwards towards the coronal section 101a of the implant member 101 and circumferentially disposed around the root section 101b of the implant member 101. In an embodiment, a temporary crown 104 is optionally placed on the dental implant 100 during the healing period when the dental implant 100 is bio-integrated with the periodontal bone structure 103c illustrated in FIG. 1A, and thereafter replaced by a permanent crown 104. The temporary crown 104 is loaded on the coronal section 101a of the implant member 101, abutting the coronal surface 101i of the coronal section 101a of the dental implant 100.

FIG. 1C exemplarily illustrates an enlarged view of the hook shaped micro-extension 101h disposed on the root section 101b of the implant member 101 of the dental implant 100. The hook shaped micro-extension 101h provides a retentive function during the initial stages of the dental implant 100.

FIG. 1D exemplarily illustrates an enlarged view of another hook shaped micro-extension 101h disposed on the root section 101b of the implant member 101 of the dental implant 100. The hook shaped micro-extension 101h provides a retentive function during the initial stages of the dental implant 100.

Figure 1E:
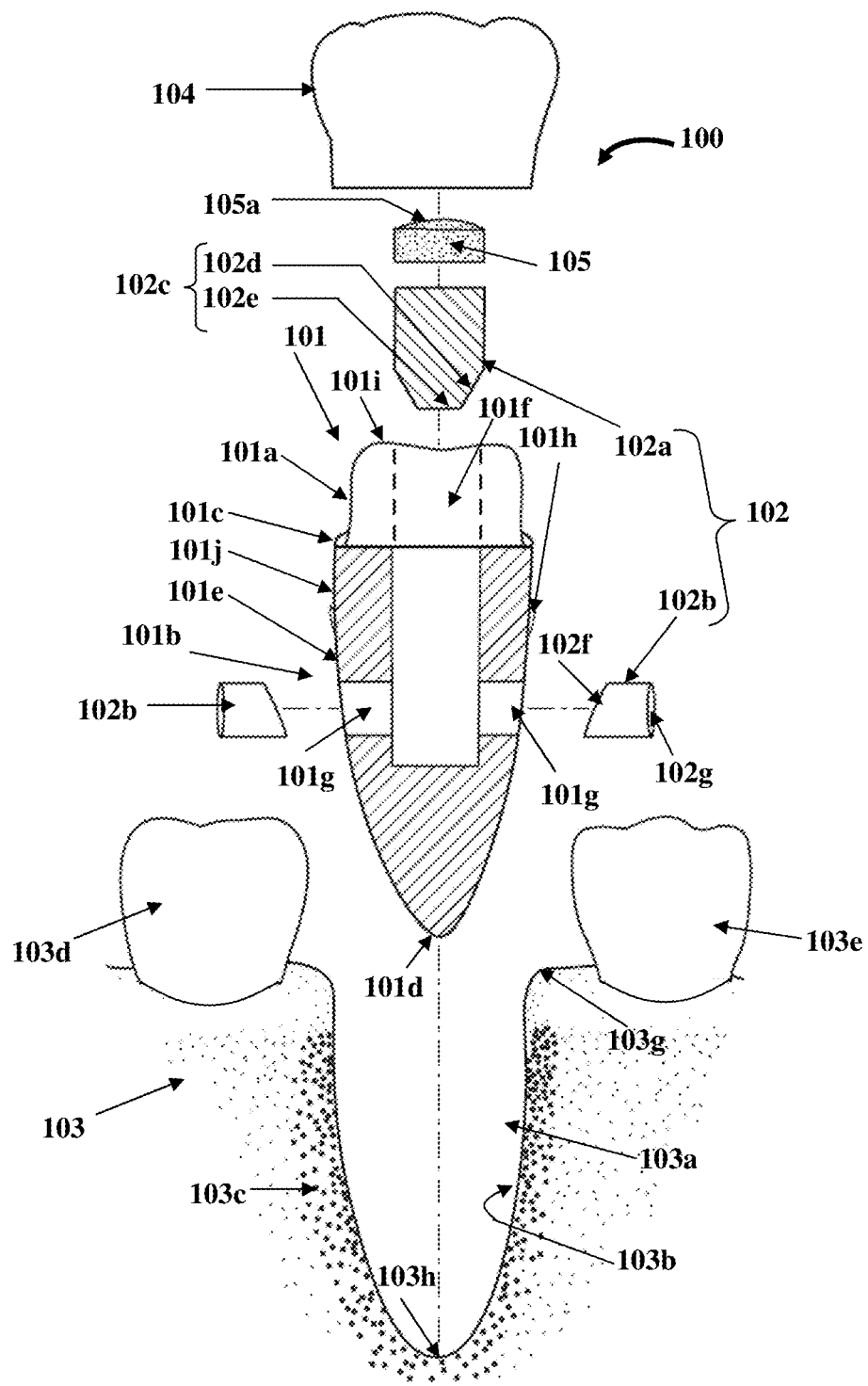
FIG. 1E exemplarily illustrates an exploded front view of the dental implant.

FIG. 1E exemplarily illustrates an exploded front view of the dental implant 100. As seen in the unassembled view of the dental implant 100 in FIG. 1E, the hollow axial cavity 101f of the implant member 101 is in fluid communication with each of the radial through-holes 101g in the implant member 101. Unlike a conventional implant design, where the dental implant 100 and the coronal section 101a are originally separate but are connected to each other at a later stage through a screw retained abutment, the root section 101b of the dental implant 100 disclosed herein and the coronal section 101a are directly connected to each other as exemplarily illustrated in FIG. 1E. The components, for example, the composite packing 105, the first fastening element 102a and the cylindrical members 102b of the anchoring assembly 102 are disclosed in the detailed description of FIG. 1A.

Figure 1F:
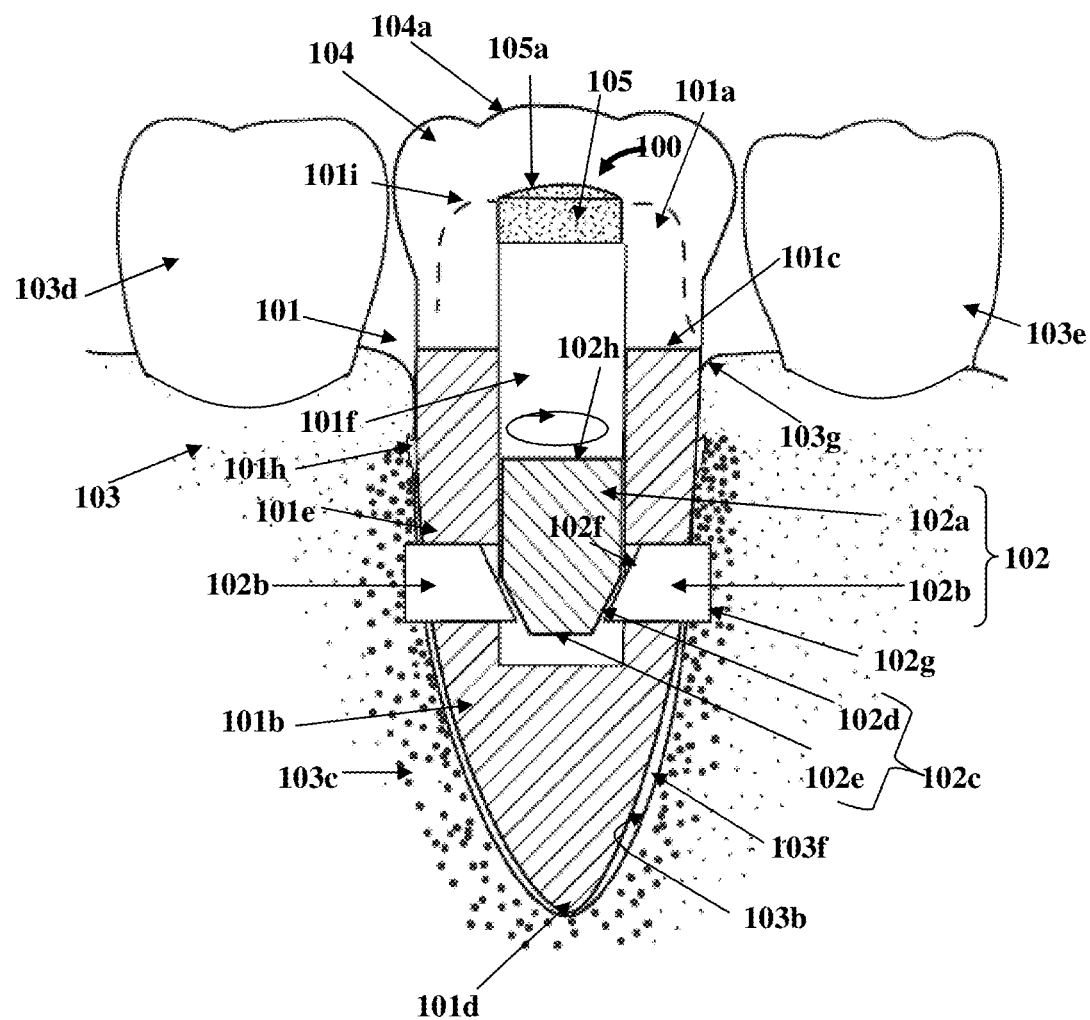
FIG. 1F exemplarily illustrates an assembled front view of the dental implant.

FIG. 1F exemplarily illustrates an assembled front view of the dental implant 100. The first fastening element 102a of the anchoring assembly 102 comprises a coronal screw head 102h and a frustoconical apical section 102c having a truncated end 102e that allows the first fastening element 102a to be advanced down or retracted up the hollow axial cavity 101f of the implant member 101 to generate an appropriate anchoring force of the cylindrical members 102b against the periodontal bone surface 103b. In an embodiment, the first fastening element 102a is threaded to screwably engage the hollow axial cavity 101f of the implant member 101. As illustrated in FIG. 1B and FIG. 1F, the first fastening element 102a apically advances within the hollow axial cavity 101f when turned by the coronal screw head 102h. When the first fastening element 102a is apically advanced within the hollow axial cavity 101f of the implant member 101, the conical shaft 102d of the first fastening element 102a radially and outwardly pushes the cylindrical members 102b through the through-holes 101g, whereby the second end 102g of each of the cylindrical members 102b abuts and evenly presses against the periodontal bone surface 103b to substantially uniformly contact the periodontal bone surface 103b and to generate an anchoring force to anchor the implant member 101 to the periodontal bone surface 103b within the periodontal bone socket 103a. The first fastening element 102a enables a dentist to precisely control the anchoring force generated by the cylindrical members 102b against the periodontal bone surface 103b by turning the coronal screw head 102h of the first fastening element 102a. In an embodiment, the amount of anchoring force is determined based on the type of bone of the patient and the bone density around the periodontal bone socket 103a illustrated in FIG. 1A and FIG. 1E, which can be estimated using three-dimensional X-ray image data captured during the treatment planning stages.

Figure 1G:
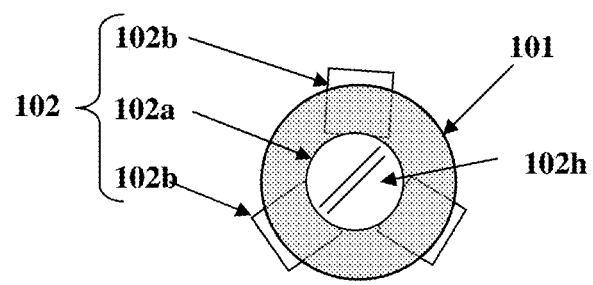
FIG. 1G exemplarily illustrates a top sectional view of the dental implant.

FIG. 1G exemplarily illustrates a top sectional view of the dental implant 100. A dentist turns the coronal screw head 102h of the first fastening element 102a, as illustrated in FIG. 1G, for controlling the anchoring force generated by the cylindrical members 102b against the periodontal bone surface 103b as exemplarily illustrated in FIG. 1F. As seen in FIG. 1F, the anchoring assembly 102 of the dental implant 100 disclosed herein functions as an inner-lock structure near the mid-portion 101e of the root section 101b of the implant member 101 to provide strong initial stability to the dental implant 100. The contact areas of the cylindrical members 102b with the periodontal bone surface 103b illustrated in FIG. 1F are roughened to provide friction and prevent slippage of the cylindrical members 102b over the periodontal bone surface 103b.

As illustrated in FIG. 1F, an interstitial space 103f defined between the outer surface 101j of the implant member 101 and the periodontal bone surface 103b is pre-planned using the X-ray images of the periodontal bone socket 103a illustrated in FIG. 1A and FIG. 1E to allow for the proper insertion of the dental implant 100 and to maintain the initial stability of the dental implant 100. The implant member 101 is designed such that the resulting interstitial space 103f after the insertion of the dental implant 100 is narrow, for example, about 30 µm at the coronal end 101c and the apical end 101d of the root section 101b, and wider, for example, about 90 µm at the mid-portion 101e of the root section 101b, which is about one-third the area of the interstitial space 103f. The narrow interstitial space 103f at the coronal end 101c and the apical end 101d of the root section 101b does not interfere with the insertion of the dental implant 100 until the final seating of the dental implant 100 in the periodontal bone socket 103a. The wider middle interstitial area 103f allows proper and trouble-free insertion of the dental implant 100. The insertion of the conical apical end 101d of the root section 101b terminates at the base 103h of the periodontal bone socket 103a as illustrated in FIG. 1A and FIG. 1E. The tighter coronal end 101c establishes a coronal seal that stabilizes the dental implant 100 at the final seating position of the dental implant 100 within the periodontal bone socket 103a, illustrated in FIG. 1A and FIG. 1E, and provides a tight seal between the dental implant 100 and the soft tissue of the periodontal bone socket 103a near the gum line 103g.

Figure 2:
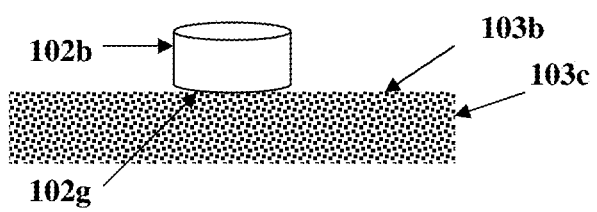
FIG. 2 exemplarily illustrates a cylindrical member of an anchoring assembly of the dental implant interfacing with a periodontal bone surface.

FIG. 2 exemplarily illustrates a cylindrical member 102b of the anchoring assembly 102 of the dental implant 100 interfacing with the periodontal bone surface 103b. The second end 102g of three equidistant cylindrical members 102b illustrated in FIG. 1G abut against and substantially uniformly contact the periodontal bone surface 103b on the periodontal bone structure 103c. The second end 102g of the equidistant cylindrical member 102b does not penetrate the periodontal bone structure 103c. The amount of anchoring force exerted by the cylindrical members 102b against the supporting periodontal bone structure 103c is controlled by the coronal screw head 102h of the first fastening element 102a, as illustrated in FIG. 1G. Controlling the anchoring force exerted by the cylindrical members 102b against the supporting periodontal bone structure 103c prevents uneven pressure and uncontrolled forces on the supporting periodontal bone structure 103c which has a tendency to damage the supporting periodontal bone structure 103c or cause necrosis of the bone, resulting in loss of tightness and retention of the dental implant 100.

Figure 3A:
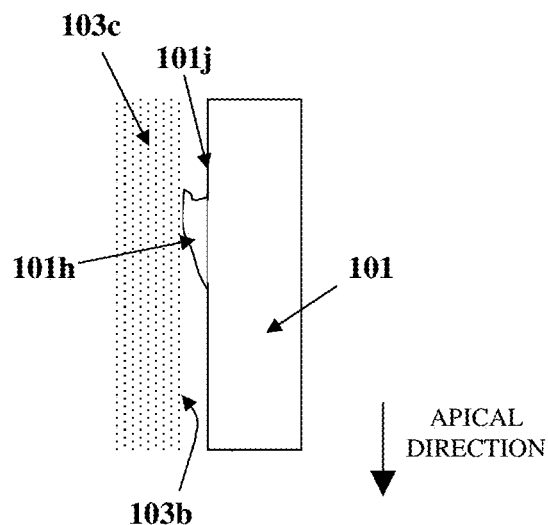
FIGS. 3A exemplarily illustrates a hook shaped micro-extension on an outer surface of an implant member of a dental implant.

FIG. 3A exemplarily illustrates a hook shaped micro-extension 101h on an outer surface 101j of the implant member 101 of the dental implant 100. The hook shaped micro-extension 101h is circumferentially disposed on the outer surface 101j of the root section 101b of the implant member 101 as exemplarily illustrated in FIGS. 1A-1B. These hook shaped micro-extensions 101h provide a retentive function during the initial stages of the dental implant 100. Typically, the hook shaped micro-extensions 101h are, for example, about 300 µm long, about 100 µm wide, and about 60 µm high. The hook shaped micro-extensions 101h are bent upwardly and therefore allow the initial movement and insertion of the implant member 101 towards the periodontal bone structure 103c without resistance. This requires that the height of the hook shaped micro-extensions 101h establishes an implant diameter slightly wider than the diameter of the periodontal bone socket 103a, for example, less than about 30 μm to about 60 μm wider than the diameter of the periodontal bone socket 103a illustrated in FIG. 1A and FIG. 1E. As these hook shaped micro-extensions 101h are disposed along the mid-portion 101e of the root section 101b of the implant member 101, the resistance to the initial apical movement at the start of the insertion of the implant member 101 in the periodontal bone socket 103a is minimal.

The hook shaped micro-extensions 101h are positioned on the outer surface 101j of the implant member 101. After the insertion of the dental implant 100 into the periodontal bone socket 103a illustrated in FIG. 1A and FIG. 1E, the hook shaped micro-extensions 101h anchor onto the periodontal bone surface 103b for impeding coronal movement of the inserted implant member 101 within the periodontal bone socket 103a as exemplarily illustrated in FIG. 1F. This allows the dental implant 100 to snap onto the periodontal bone socket 103a after the insertion to maximize the retention of the dental implant 100 in the periodontal bone socket 103a and to establish the initial stability of the dental implant 100. After the insertion of the dental implant 100, the tips of these hook shaped micro-extensions 101h reach very close, for example, about 30 μm to the supporting periodontal bone structure 103c, thereby providing resistance to backward coronal movement of the implant member 101. Hence, during the initial stages of the dental implant 100, the hook shaped micro-extensions 101h prevent the dental implant 100 from dislodging out of the periodontal bone socket 103a. On the other hand, when a patient applies an apical biting force towards the base 103h of the periodontal bone socket 103a, the hook shaped micro-extensions 101h do not interfere with such apical forces. In an embodiment, isolated or contiguous groups of these hook shaped micro-extensions 101h are added over the root section 101b of the implant member 101. In another embodiment, the hook shaped micro-extensions 101h are much smaller and are etched over the ridges 403 of grooves 401 on the root section 101b of the implant member 101 as exemplarily illustrated in FIG. 4A and FIG. 6A respectively.

Figure 3B:
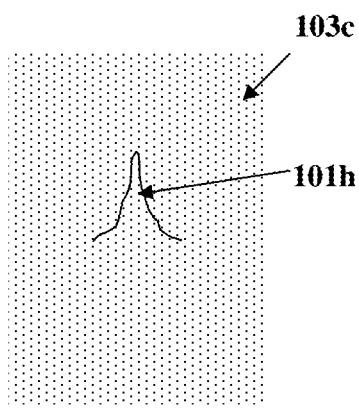
FIG. 3B exemplarily illustrates another hook shaped micro-extension on the outer surface of the implant member of the dental implant.

FIG. 3B exemplarily illustrates another hook shaped micro-extension 101h on an outer surface 101j of the implant member 101 of the dental implant 100. The hook shaped micro-extension 101h is circumferentially disposed on the outer surface 101j of the root section 101b of the implant member 101 as exemplarily illustrated in FIGS. 1A-1B. The height of the hook shaped extensions 101h also varies with the bone density. If the bone density is low, the implant member 101 with higher hook shaped extensions 101h are inserted into the periodontal bone socket 103a and provides strong retention with the supporting bone structure.

Figure 4A:
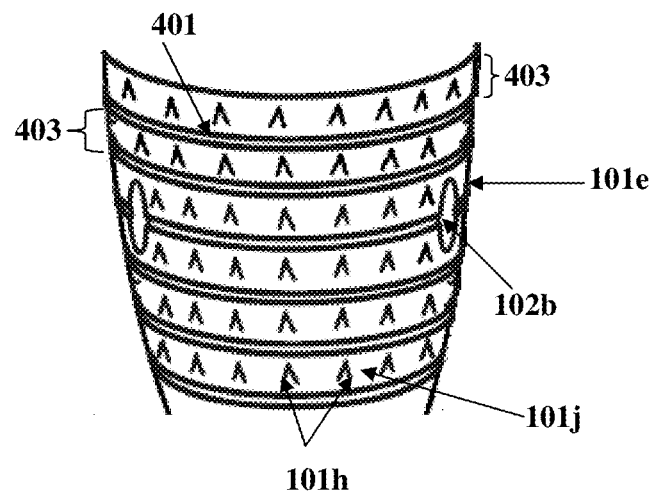
FIG. 4A exemplarily illustrates retentive grooves on the outer surface of the implant member along a root section of the implant member.
Figure 4B:
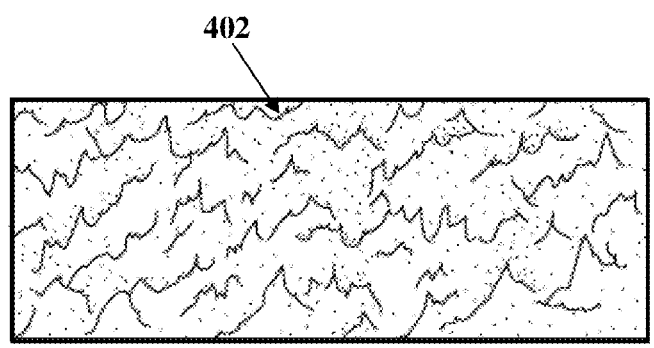
FIG. 4B exemplarily illustrates a sandblasted micro-textured outer surface of the implant member.
Figures 6A, 6B:
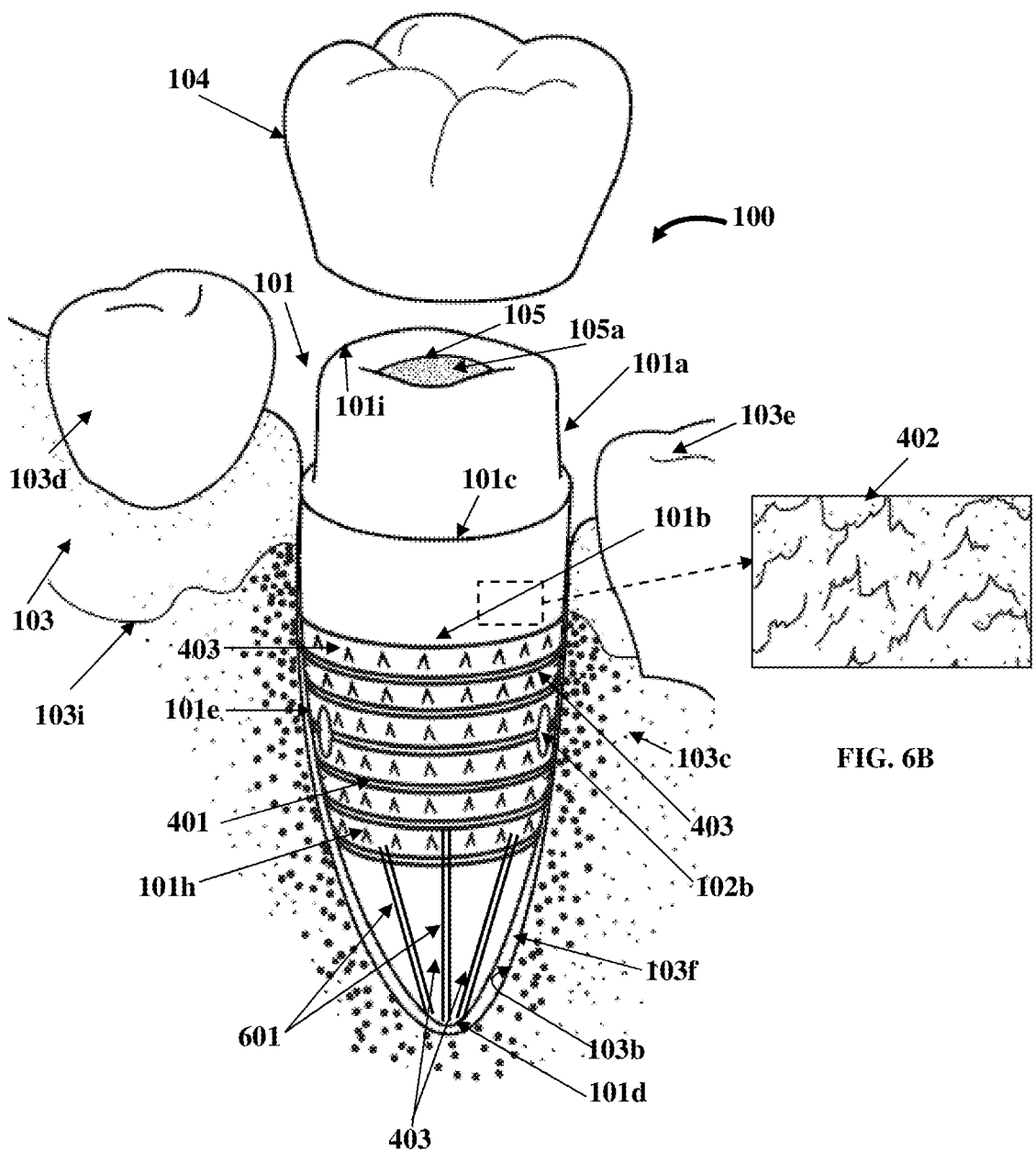
FIG. 6A exemplarily illustrates loading of a permanent crown and/or a pre-fabricated tooth colored layer over the coronal surface of the implant member of the dental implant.
FIG. 6B exemplarily illustrates an enlarged view of the sandblasted micro-textured outer surface of the implant member.

FIG. 4A exemplarily illustrates retentive grooves 401 on the outer surface 101j of the implant member 101 along the root section 101b of the implant member 101. The outer surface 101j of the implant member 101 is a sandblasted micro-textured surface 402. In an embodiment, if the sandblasted micro-textured surface 402 of the implant member 101 is above the periodontal bone socket 103a, provides a smooth surface without the sandblasted micro-texture thereby avoiding microorganisms colonize on the sandblasted micro-texture surface 402 of the implant member 101. In another embodiment, if the sandblasted micro-textured surface 402 of the implant member 101 is below the periodontal bone socket 103a, provides a surface with the sandblasted micro-texture as exemplarily illustrated in FIG. 4B. Although, initially the periodontal bone structure 103c illustrated in FIG. 1A and FIGS. 1E-1F are not integrated with the dental implant 100, the interstitial space 103f of from about 30 μm to about 90 μm is filled, for example, with micro bone filler materials. These bone filler materials are gradually replaced by real bone tissues, when the dental implant 100 is bio-integrated with the supporting periodontal bone structure 103c. Hence, the dental implant 100 incorporates the sandblasted surface structure 402 and the retentive grooves 401 on the implant member 101 to increase the contact area between the implant member 101 and the periodontal bone surface 103b illustrated in FIG. 1A and FIGS. 1E-1F, and to engage the dental implant 100 in the periodontal bone socket 103a of the periodontal bone structure 103c. The retentive grooves 401 illustrated in FIG. 4A ensure the long term stability and longevity of the dental implant 100. The retentive grooves 401 are provided along the mid-portion 101e of the root section 101b of the implant member 101 to increase the contact area between the implant member 101 and the periodontal bone surface 103b as exemplarily illustrated in FIG. 4A and FIG. 6A. The retentive grooves 401 are disposed either parallel to each other or spirally wound around the mid-portion 101e of the root section 101b of the implant member 101. The deep retentive grooves 401 illustrated in FIG. 4A derive support from the periodontal bone structure 103c against biting forces and prevent the dental implant 100 disclosed herein from dislodging out of the periodontal bone socket 103a. As the bone filler materials in the retentive grooves 401 are replaced by natural bone structures, the retentive grooves 401 provide the same support as a conventional implant design. In an embodiment, the ridges 403 of the retentive grooves 401 provided over the mid-portion 101e of the root section 101b of the implant member 101 are etched with the hook shaped micro-extensions 101h, as illustrated in FIG. 4A and FIG. 6A. As illustrated in FIG. 4B and FIG. 6B, the outer surface 101j of the implant member 101, specifically those areas in contact with the periodontal bone surface 103b are sandblasted to produce the sandblasted micro-textured surface 402 on the implant member 101. The sandblasted micro-textured surface 402 further increases the contact area between the dental implant 100 and the periodontal bone surface 103b, and allows the periodontal bone structure 103c, tissue and fibers such as Sharpie's fibers to grow and anchor onto the sandblasted micro-textured surface 402 of the implant member 101. The hook shaped extensions 101h provides an initial stability, and allows a new bone to form inside the retentive grooves 401 resulting in the long term stability of the dental implant 100.

In order to ensure bone growth around the dental implant 100, agents that encourage bone growth, for example, osteogenic materials and antibiotic agents that prevent infection are mixed with the bone filler material. The tapered inner canal 1101 of the implant member 101 delivers osteogenic materials and antibiotic agents. The interstitial space 103f illustrated in FIG. 1F is filled with the bone filler material, the osteogenic material, and the antibiotic agents to ensure bone regeneration and long term stability of the dental implant 100. The osteogenic materials in the interstitial space 103f and in the retentive grooves 401 of the implant member 101 induce bone into the retentive grooves 401 and ensure long term stability of the dental implant 100.

Proper soft tissue health around the dental implant 100 is important in preventing infections in and around the periodontal bone socket 103a. The areas of the dental implant 100 that are in contact with soft periodontal tissues are polished and smoothed to prevent plaque and calculus accumulation. The depth of the soft periodontal tissue layer can be determined from X-ray imaging, and is typically around 2 mm from the underline bone level 1031 illustrated in FIG. 6A. In case of esthetically prominent teeth such as incisors and canines, a dark surface of the implant member 101 produces a visible dark halo through the gingiva. In such a case, a white coating can be provided in the soft periodontal tissue layer to produce an esthetic result. Compared to the diameter of the natural tooth, the cross-sectional area of the implant member 101 is made slightly larger, about 20 μm larger, to provide a tight seal and prevent foreign bodies from entering into the interstitial space 103f between the implant member 101 and the periodontal bone surface 103b. Since the implant member 101 connects from the bone to the tissue level, and to the open oral cavity, the surface of the implant member 101 is exposed to abrasion and oxidation from the oxygen in the air. Therefore, in an embodiment, the implant member 101 is manufactured from materials that are non-poisonous and chemically inert. For example, titanium oxide is toxic to humans, and hence not used to fabricate the implant member 101. Zirconium oxide is used in the intra oral application, and not toxic to humans. Therefore Zirconium is used instead of Titanium in the clinical settings to avoid possible toxic oxidation of the implant surface.

Figure 5:
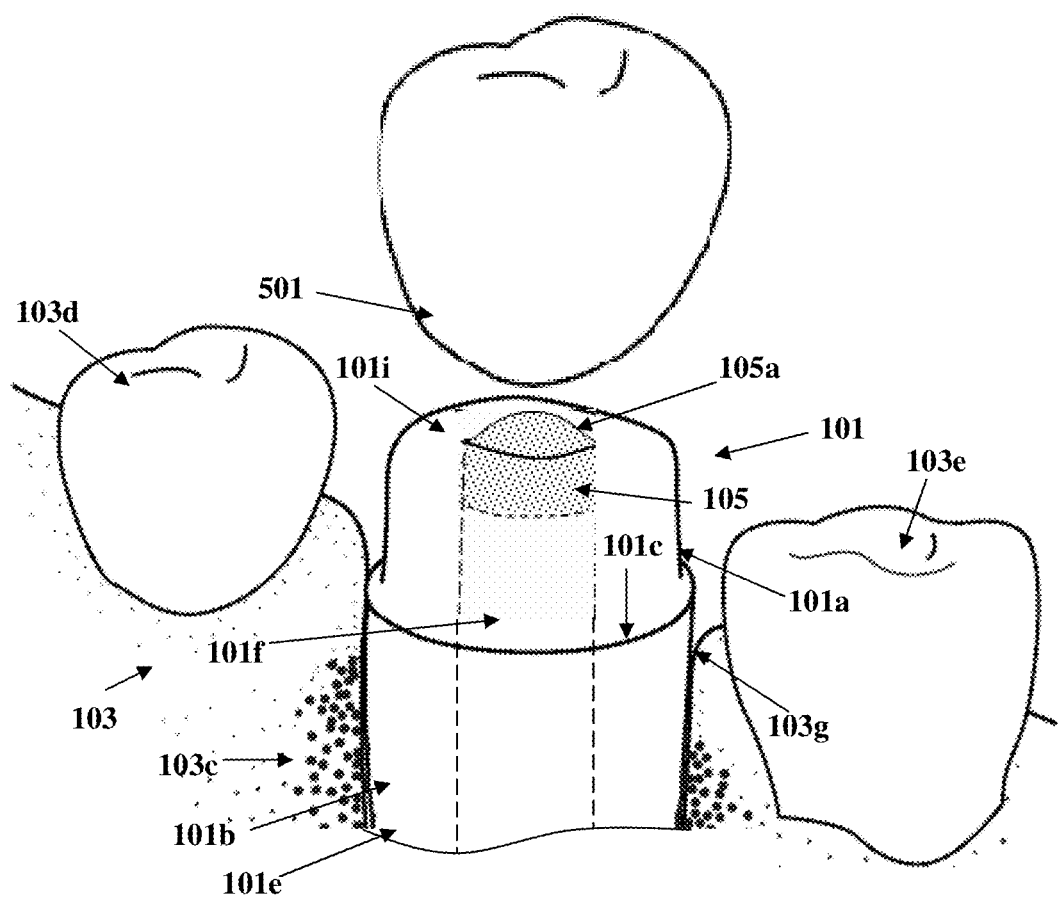
FIG. 5 exemplarily illustrates a coronal surface of the implant member of the dental implant, showing a composite packing.

FIG. 5 exemplarily illustrates a coronal surface 101i of the implant member 101 dental implant 100, showing a composite packing 105. During the first several months, in order to provide an optimal environment for the periodontal bone structure 103c to bio-integrate with the implant member 101, the coronal section 101a is designed to avoid direct contact with the opposing teeth 501, especially para-functional interferences. The composite packing 105 is provided to avoid direct contact of the coronal section 101a of the implant member 101 with the opposing teeth 501. As illustrated in FIG. 1F, either a temporary crown or a permanent crown 104 is placed over the composite packing 105. The temporary crown 104 will not be in contact with the opposing teeth 501 so that the dental implant 100 is not subjected to any forces during bio-integration. At the completion of the bio-integration between the dental implant 100 and the periodontal bone structure 103c, the biting surface of the coronal section 101a of the dental implant 100, herein referred to as the coronal surface 101i can be modified to restore the proper contact between the opposing upper and lower teeth 501. As illustrated in FIG. 5, the coronal surface 101i of the implant member 101, where the opposing upper and lower teeth 501 make contact, comprises the composite packing 105 that is filled with tooth filling composite materials. The composite packing 105 is a pre-designed cartridge that avoids direct occlusal contact of the implant member 101 with the opposing teeth 501 to reduce para-functional interferences during the osseointegration period of the dental implant 100. The composite packing 105 can be removed and refilled to a higher surface level 105a to contact the opposing tooth surface 501 at a later stage.

In many cases, where the opposite teeth 501 are natural teeth, the natural teeth 501 tends to shift down and contact the coronal surface 101i or the composite packing 105 over a period of time, corresponding to the period of bio-integration of the dental implant 100. In such cases, occlusal modifications at the end of the bio-integration are eliminated.

In an embodiment, areas of the coronal surface 101i of the coronal section 101a of the implant member 101 that are exposed to the oral cavity are coated with tooth colored materials such as Zirconia oxide. The shade or color of the surface coating on the coronal surface 101i is chosen to match the original shade or color of the natural teeth. Layers of translucent and opaque material are overlaid on top of each other to ensure a natural tooth appearance.

In some cases, a tooth colored layer 104 is fabricated separately similar to a conventional crown, and cemented or screw-retained to the dental implant 100. In these cases, the coronal section 101a of the implant member 101 projecting over the gum line 103g is designed and prepared similar to a prepared tooth surface for loading a dental crown 104, as illustrated in FIG. 6A. FIG. 6A exemplarily illustrates loading of a permanent crown 104 and/or a pre-fabricated tooth colored layer over the coronal surface 101i of the implant member 101 of the dental implant 100. In another embodiment, temporary crowns 104 are placed during the healing period before the dental implant 100 is bio-integrated with the supporting periodontal bone structure 103c, and thereafter replaced by a permanent crown 104. These crowns 104 can be retained, for example, using dental cement or screws that can be accessed from the occlusal surface 104a of the crowns 104 and filled with a composite. As used herein, the occlusal surface 104a refers to the surface of the crown 104 that makes occlusal contact with the opposing teeth 501. In case of temporary crowns 104, the coronal surface 101i is designed to avoid occlusal contact with the opposing teeth surface.

Figure 10:
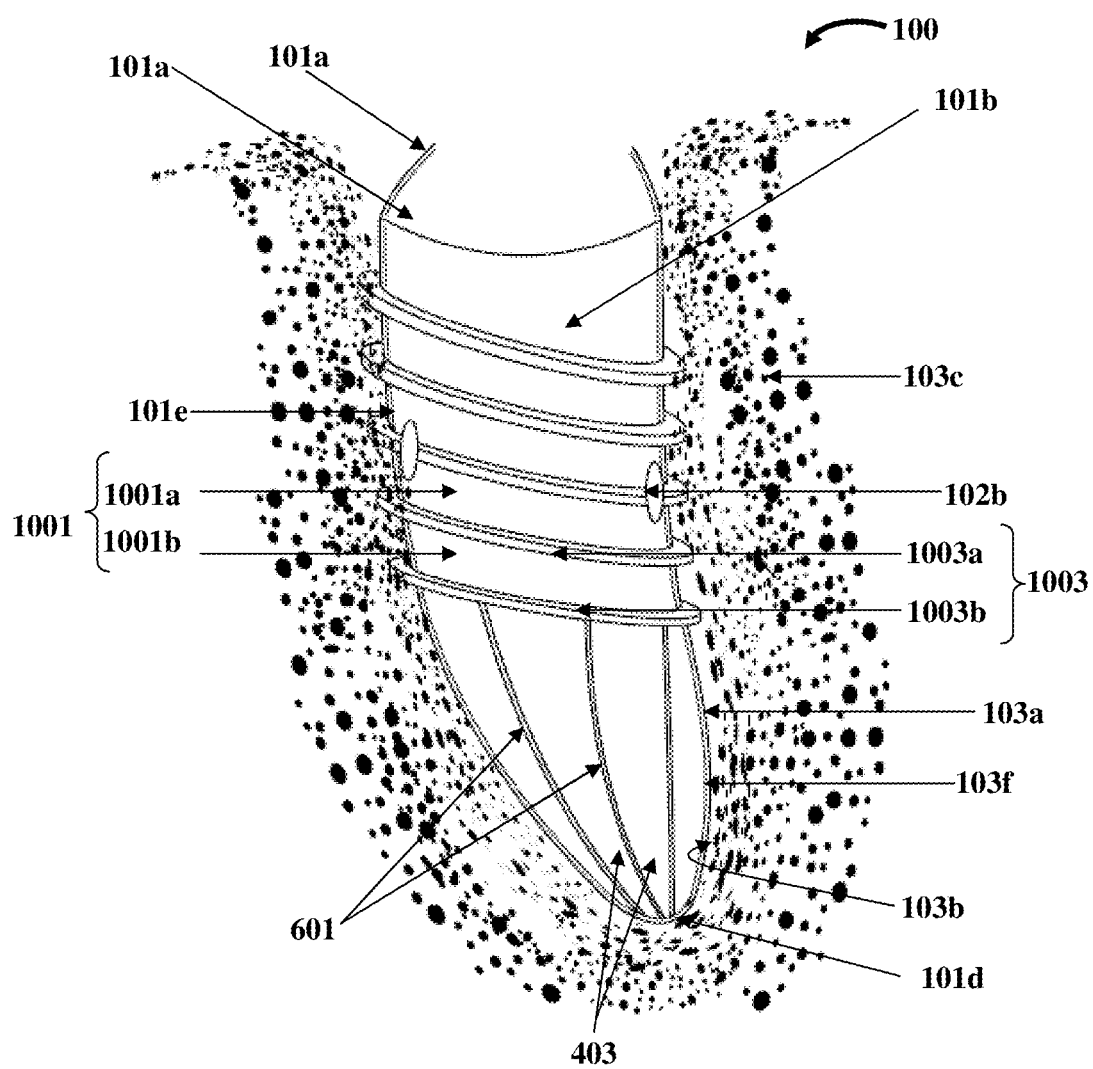
FIG. 10 exemplarily illustrates an alternative embodiment of the implant member comprising retentive spiral grooves diagonal to the periodontal bone socket.

In an embodiment, the implant member 101 further comprises one or more longitudinal grooves 601 as illustrated in FIG. 6A. The longitudinal grooves 601 are provided on the implant member 101 substantially parallel to the periodontal bone socket 103a for allowing debris to escape out of the periodontal bone socket 103a during the insertion of the implant member 101 within the periodontal bone socket 103a. FIG. 6B exemplarily illustrates an enlarged view of the sandblasted micro-textured outer surface 402 of the implant member 101. In another embodiment, as illustrated in FIG. 10, the implant member 101 further comprises one or more spiral grooves 1001.

Figure 7:
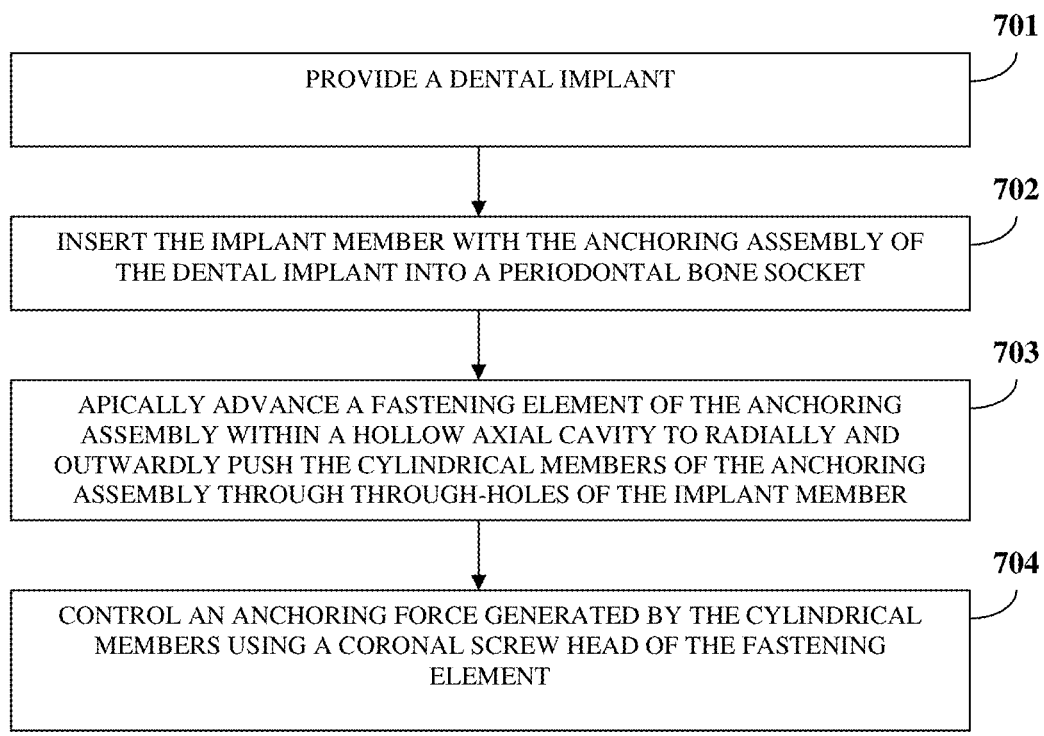
FIG. 7 illustrates a method for installing a dental implant.

FIG. 7 illustrates a method for installing a dental implant 100. The dental implant 100, as disclosed in the detailed description of FIGS. 1A-1E, is provided 701. Before the insertion of the dental implant 100, atraumatic extraction is performed to minimize the damages to the surrounding periodontal bone structure 103c and soft tissue. All infected and inflamed tissues in the periodontal bone socket 103a are removed before the insertion of the dental implant 100. The implant member 101 with the anchoring assembly 102 of the dental implant 100 is inserted 702 into the periodontal bone socket 103a of the patient. A proper initial orientation of the dental implant 100 is important to ensure that the dental implant 100 follows the correct insertion path in the first attempt, such that the dental implant 100 need not be removed and reinserted again. Due to a resistance mechanism along the outer surface 101j of the implant member 101, if the dental implant 100 is inserted in the wrong orientation, the dental implant 100 locks itself in the periodontal bone socket 103a after insertion. In such a case, it might be difficult to extract the dental implant 100 without damaging the periodontal bone surface 103b. The anatomy of the crown 104 of the teeth should properly guide an experienced dentist to place the dental implant 100 in the correct initial orientation. Once the dental implant 100 is correctly and fully seated in the periodontal bone socket 103a, the first fastening element 102a of the anchoring assembly 102 is apically advanced 703 within the hollow axial cavity 101f of the implant member 101. The conical shaft 102d of the first fastening element 102a radially and outwardly pushes the cylindrical members 102b of the anchoring assembly 102 through the through-holes 101g and presses the second end 102g of each of the cylindrical members 102b substantially uniformly against the periodontal bone surface 103b to generate an anchoring force to anchor the implant member 101 within the periodontal bone socket 103a.

In an embodiment, the first fastening element 102a is threaded to screwably engage the hollow axial cavity 101f of the implant member 101. The first fastening element 102a comprises a coronal screw head 102h for tightening or releasing the first fastening element 102a within the hollow axial cavity 101f. The first fastening element 102a is apically advanced within the hollow axial cavity 101f by turning the coronal screw head 102h of the first fastening element 102a. The method disclosed herein enables a dentist to precisely control 704 the anchoring force generated by the cylindrical members 102b using the coronal screw head 102h of the first fastening element 102a.

As exemplarily illustrated in FIGS. 1A-1E, multiple hook shaped micro-extensions 101h are fabricated to point upwards towards the coronal section 101a of the implant member 101. The multiple hook shaped micro-extensions 101h are circumferentially disposed around the root section 101b of the implant member 101 for impeding coronal movement of the inserted implant member 101 within the periodontal bone socket 103a. As illustrated in FIG. 4B, an outer surface 101j of the implant member 101 is sandblasted to obtain a sandblasted micro-textured surface 402. The outer surface 101j is also provided with retentive grooves 401 along the root section 101b of the implant member 101 to increase the contact area between the implant member 101 and the periodontal bone surface 103b. As illustrated in FIG. 6A, one or more longitudinal grooves 601 are provided on the implant member 101 parallel to the periodontal bone socket 103a for allowing excess bone filler material and debris to escape out of the periodontal bone socket 103a during the insertion of the implant member 101 within the periodontal bone socket 103a.

FIG. 10 exemplarily illustrates an alternative embodiment of the implant member 101 comprising retentive spiral grooves 1001, for example retentive spiral grooves 1001a and 1001b, diagonal to the periodontal bone socket 103a. The implant member 101 shown in FIG. 10 further comprises spiral ridges 1003a and 1003b adjacent to the retentive spiral grooves 1001a and 1001b on a mid-portion 101e of the root section 101b of the dental implant 100. The spiral grooves 1001 provide an alternative option for inserting the implant member 101 into the periodontal bone socket 103a. For example, the spiral grooves 1001 enable the implant member 101 to be inserted into the periodontal bone socket 103a by rotating and advancing the implant member 101 into the periodontal bone socket 103a.

The retentive spiral grooves 1001 allow excess bone filler material and debris to escape out of the periodontal bone socket 103a during the insertion of the implant member 101 within the periodontal bone socket 103a. In an embodiment, the implant member 101 is rotated and advanced into the periodontal bone socket 103a. The spiral ridges 1003a and 1003b along the length of the implant member 101 remove the excess bone filler material and the debris from the periodontal bone socket 103a. In an embodiment, the implant member 101 further comprises one or more longitudinal grooves 601 located below the retentive spiral grooves 1001, as illustrated in FIG. 10A. The longitudinal grooves 601 are provided on the implant member 101 substantially parallel to the periodontal bone socket 103a for allowing debris to escape out of the periodontal bone socket 103a, for example, through the retentive spiral grooves 1001, during the insertion of the implant member 101 within the periodontal bone socket 103a.

After the insertion of the implant member 101, an interstitial space 103f defined between the periodontal bone surface 103b and the outer surface 101j of the implant member 101 is filled, for example, with a bone filler material, an osteogenic material, antibiotic agents, etc. to ensure bone regeneration and long term stability of the dental implant 100. A coronal surface 101i of the implant member 101 is provided with a composite packing 105 filled with tooth filling composite materials. The composite packing 105 avoids direct contact of the implant member 101 with the opposing teeth 501 as exemplarily illustrate in FIG. 5 to reduce para-functional interferences during the osseointegration period of the dental implant 100. In an embodiment, the inserted dental implant 100 is loaded with a temporary crown 104, and loaded with a permanent crown 104 after the osseointegration period. In an embodiment, the coronal surface 101i of the dental implant 100 is overlaid with one or more pre-fabricated tooth colored layers. The method for installing the dental implant 100 disclosed herein, further comprises determining one or more undercut area 1201 and one or more insufficient bone area 1202 as exemplarily illustrated in the detailed description of FIG. 12. The method disclosed herein, further comprises a traditional implant drill 1501 for drilling an additional implant space is exemplarily illustrated in the detailed description of FIG. 15.

FIGS. 1-6 disclose a dental implant 100 and FIG. 7 discloses a method for installing the dental implant 100. An alternate embodiment of the dental implant 100 comprising retentive spiral grooves 1001a and 1001b diagonal to the periodontal bone socket 103a is provided in the description of FIGS. 10, 11A and 11B. In addition, a system for fabricating the dental implant 100 with retentive spiral grooves 1001a and 1001b diagonal to the periodontal bone socket 103a is provided in the description of FIG. 8. In addition, a method for fabricating the dental implant 100 with retentive spiral grooves 1001a and 1001b diagonal to the periodontal bone socket 103a is provided in the description of FIG. 9.

Figure 8:
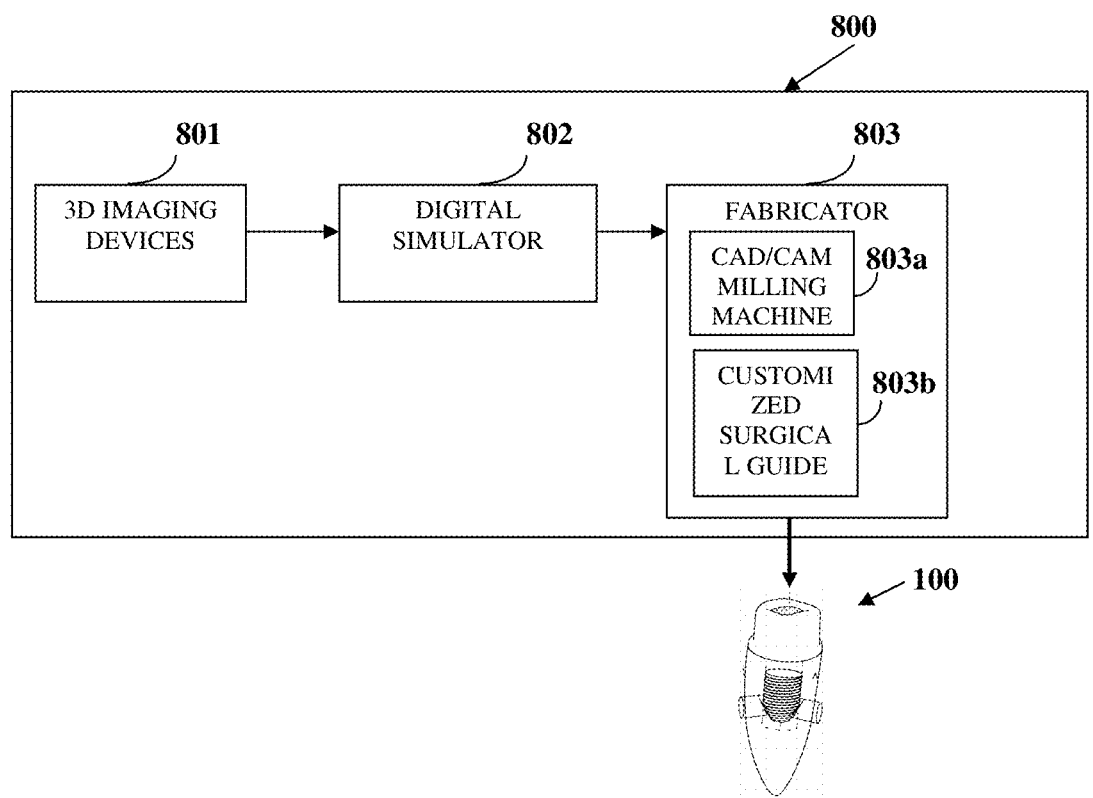
FIG. 8 exemplarily illustrates a system for fabricating a dental implant.

FIG. 8 exemplarily illustrates a system 800 for fabricating a dental implant 100. In an embodiment disclosed herein, system 800 comprises one or more three-dimensional (3D) imaging devices 801, a digital simulator 802, and a fabricator 803. The 3D imaging devices 801 capture high resolution, three-dimensional images of a natural tooth and a corresponding periodontal bone socket 103a illustrated in FIGS. 1A, 1E, 1F, 6A, 10, 11A, and 15 of the natural tooth before extraction of the natural tooth. The 3D imaging devices are for example, three-dimensional X-ray imaging device or a three-dimensional optical scanner. The digital simulator 802 digitally simulates insertion of the dental implant 100 into the periodontal bone socket 103a using the three-dimensional images to establish a path for inserting the dental implant 100. The digital stimulator 802 predetermines an anchoring force required for anchoring the designed dental implant 100 within the periodontal bone socket 103a. The fabricator 803 fabricates and mills the dental implant 100 according to a treatment plan based on the digital simulation. The fabricator 803 further comprises a computer aided design and computer aided manufacturing (CAD/CAM) milling machine 803a and a customized surgical guide 803b. As used herein, "customized surgical guide" refers to a guide that assists in precise surgical placement and angulation of the dental implant 100. Also, the customized surgical guide 803b provides an accurate placement of the dental implant 100 according to the pre-defined surgical treatment plan. The computer aided design and computer aided manufacturing (CAD/CAM) milling machine 803*a* produces fine details of the implant member 101 of the dental implant 100. The customized surgical guide 803*b* is exemplarily illustrated in the detailed description of FIG. 13 and FIGS. 14A-14C.

In an embodiment, the computer aided design and computer aided manufacturing (CAD/CAM) milling machine 803*a* is configured for designing the dental implant 100 to maintain a distance of about 1000 µm, or for example, about 500 µm to about 1200 µm, between the dental implant 100 and one or more of an adjacent nerve canal, an adjacent sinus, and an adjacent blood vessel. In an embodiment, the computer aided design and computer aided manufacturing (CAD/CAM) milling machine 803*a* is configured for designing the dental implant 100 to maintain a distance of about 100 µm to about 1500 µm between the dental implant 100 and the one or more adjacent nerve canal, the adjacent sinus, and the adjacent blood vessel. In another embodiment, the computer aided design and computer aided manufacturing (CAD/CAM) milling machine 803*a* is further configured for designing the dental implant 100 to maintain an interstitial space 103*f* of about 30 µm, or for example between 10 µm to about 60 µm, between a coronal end 101*c* and an apical end 101*d* of a root section 101*b* of the dental implant 100 and the periodontal bone socket 103*a*. Furthermore, the computer aided design and computer aided manufacturing (CAD/CAM) milling machine 803*a* is further configured for designing the dental implant 100 to maintain an interstitial space 103*f* of about 90 µm, or for example between 50 µm to about 120 µm, between a mid-portion 101*e* of the root section 101*b* of the dental implant 100 and the periodontal bone socket 103*a*. The computer aided design and computer aided manufacturing (CAD/CAM) milling machine 803*a* also creates multiple concentric retentive grooves 401 and 601 along an outer surface 101*j* of a mid-portion 101*e* of the root section 101*b* of the implant member 101, wherein adjacent grooves 401 and 601 define ridges 403 formed therebetween as illustrated in FIG. 10. In an embodiment, the computer aided design and computer aided manufacturing (CAD/CAM) milling machine 803*a* is configured to create retentive spiral grooves 1001, for example retentive spiral grooves 1001*a* and 1001*b*, diagonal to the periodontal bone socket 103*a*, as shown in FIG. 10. The computer aided design and computer aided manufacturing (CAD/CAM) milling machine 803*a* is further configured to create spiral ridges 1003*a* and 1003*b* adjacent to the retentive spiral grooves 1001*a* and 1001*b* on a mid-portion 101*e* of the root section 101*b* of the dental implant 100.

Figure 9:
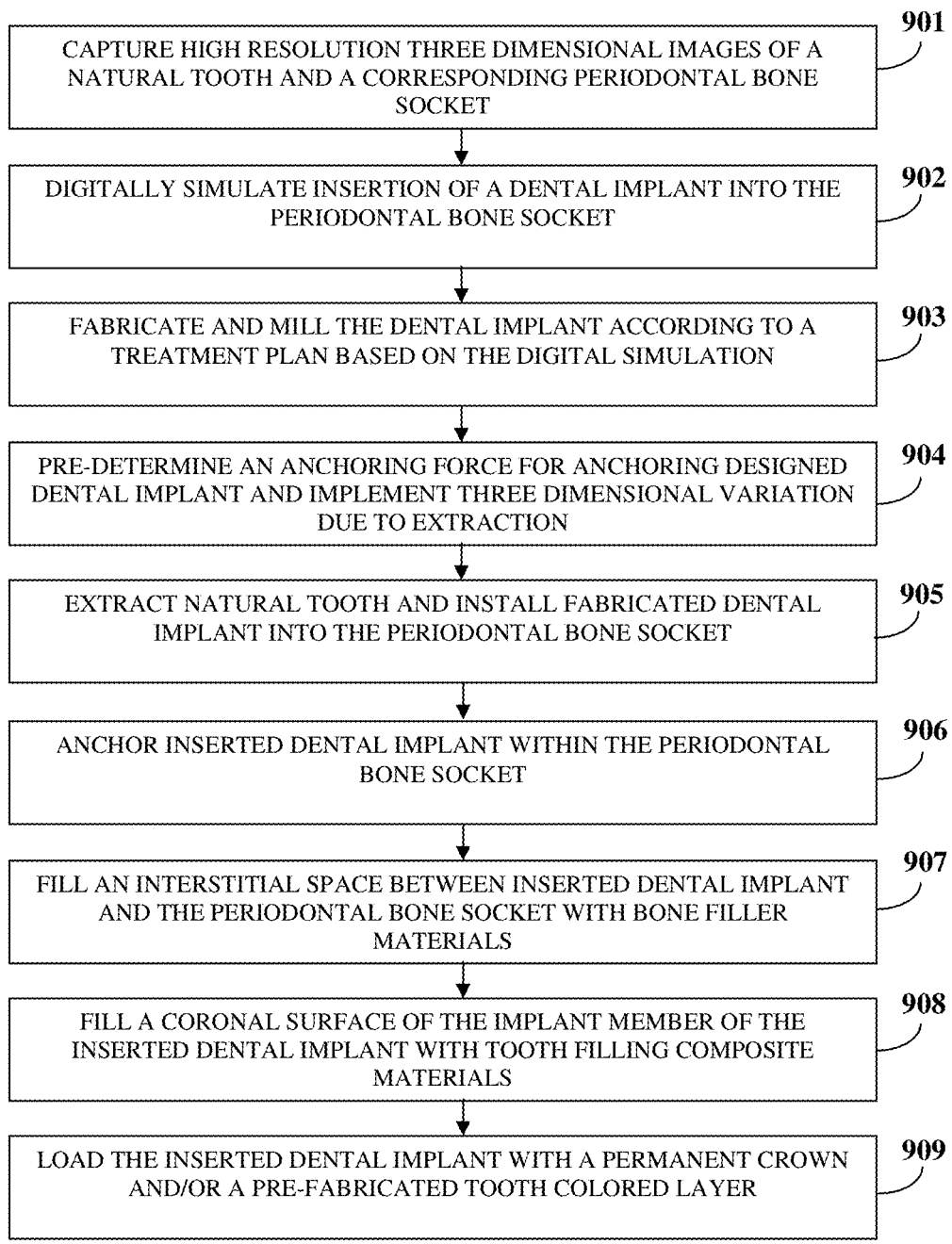
FIG. 9 exemplarily illustrates a method for fabricating a dental implant.

In an embodiment, FIG. 9 exemplarily illustrates a method for fabricating a dental implant 100. High resolution three-dimensional (3D) images of a natural tooth and a corresponding periodontal bone socket 103*a* of the natural tooth are captured 901, for example, before the extraction of the natural tooth using a three-dimensional X-ray imaging device or a three-dimensional optical scanner. In cases where there is severe tooth infection, the periodontal bone structure 103*c* around the tooth root may undergo resorption, in which case there may be a discrepancy between the X-ray image of the periodontal bone socket 103*a* and the root structure of the tooth. If the dental implant 100 is designed based on the shape of the tooth root alone and inserted into the periodontal bone socket 103*a*, an open gap is created between the implant member 101 and the periodontal bone surface 103*b* due to the resorption, and the inserted dental implant 100 may be wobbly. Hence, the dental implant 100 is configured to a shape of the image of the periodontal bone socket 103*a*, which accounts for both the root of the tooth and the resorbed portion. In order to secure the dental implant 100 firmly into the periodontal bone socket 103*a*, the shape of the dental implant 100 is configured to compensate for the discrepancy created by the resorption. Due to the extraction process, the variations of the three-dimensional shape of the periodontal bone socket 103*a* are incorporated and accounted for during the three-dimensional planning of fabricating the dental implant 100. For example, a periodontal bone socket 103*a* having a lesser bone density and that requires higher extraction force to remove a natural tooth widens during the extraction process which incorporated and accounted for during the three-dimensional planning of fabricating the dental implant 100.

Figure 18:
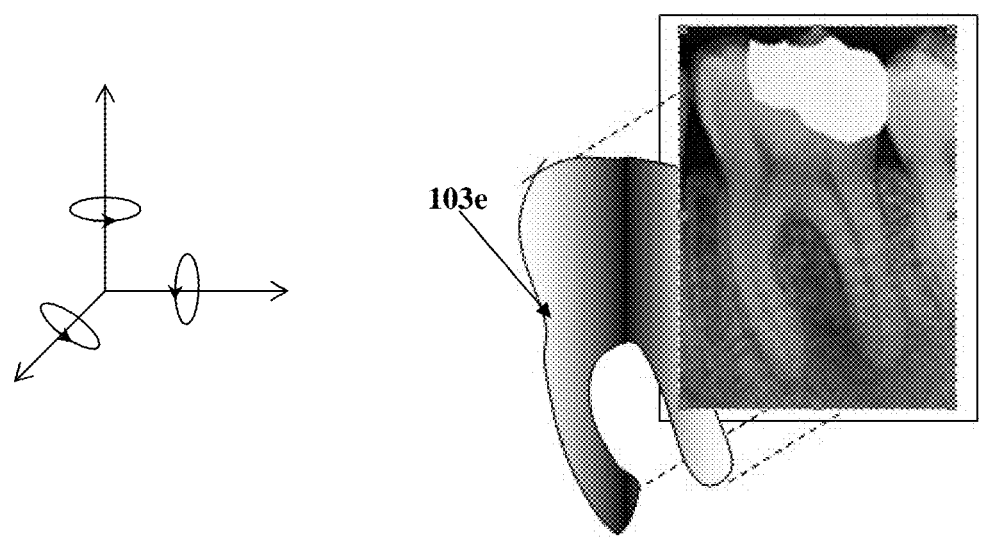
FIG. 18 exemplarily illustrates a two-dimensional peri-apical image taken at different angles of the natural tooth.
Figure 19:
FIG. 19 exemplarily illustrates a series of exponential functions for parameterizing the root of the natural tooth.

In an embodiment, the captured high-resolution three-dimensional images of the natural tooth is further enhanced using a two-dimensional periapical X-ray image by overlapping the captured high-resolution three-dimensional images with the two-dimensional periapical X-ray image of the natural tooth as exemplarily illustrated in FIG. 18. The two-dimensional periapical X-ray image is further configured for converting a density function of the captured one or more three-dimensional images to a density function of the two-dimensional periapical X-ray images, thereby improving the resolution of the captured three-dimensional images of the natural tooth, as exemplarily illustrated in FIGS. 19 and 20.

In an embodiment, the interstitial space around a natural tooth is about 200 µm in width. This interstitial space is filled with periodontal tissue such as ligaments to limit tooth movement. As illustrated in FIG. 10, if an interstitial space 103*f* of over 200 µm is allowed between the periodontal bone surface 103*b* and the dental implant 100, in a dental implant 100, micro-organisms such as bacteria access the interstitial space 103*f*. Furthermore, a greater interstitial space 103*f* between the periodontal bone surface 103*b* and the dental implant 100 the dental implant 100 may dislodge from the periodontal bone socket 103*a* due to movement allowed by the greater interstitial space 103*f*. Accordingly, a much narrower interstitial space 103*f* between the dental implant 100 and the periodontal bone surface 103*b* is defined, especially near the coronal end 101*c* of the root section 101*b* of the implant member 101 where the dental implant 100 is exposed to the oral cavity. The narrow interstitial space 103*f* between the dental implant 100 and the periodontal bone surface 103*b* firmly anchors the dental implant 100 inside the periodontal bone structure 103*c* for a longer period of time. Accordingly, a high-resolution three-dimensional X-ray of, for example, about 30 µm is acquired to determine the exact dimensions of the tooth and the periodontal bone socket 103*a* in designing the dental implant 100.

In an embodiment, tooth shade or color scan is also obtained from the natural tooth/teeth. The digital information comprising the high resolution X-ray images and the color scan is sent to a dental lab to custom build a customized dental implant 100 for the tooth to be replaced. Using this digital information, the root section 101*b* of the implant member 101 of the dental implant 100 is fabricated to resemble the shape of the root of the natural tooth. The shade of the coronal section 101*a* of the implant member 101 of the dental implant 100 is fabricated to match the natural shade of the tooth. Some of the factors considered in the customized construction of the dental implant 100 and the restoration comprise proper insertion, initial stability, long-term stability, and functional and esthetic factors.

In an embodiment, the three-dimensional images are used to digitally simulate 902 the insertion of the dental implant 100 into the periodontal bone socket 103a to establish a path for inserting the dental implant 100. The pre-surgical three-dimensional (3D) image simulation is performed to ensure proper insertion of the dental implant 100 into the periodontal bone socket 103a. The path of insertion of the dental implant 100 is established to avoid any undercuts that may block the insertion of the dental implant 100. If the implant member 101 of the dental implant 100 is to be positioned within about 1000 µm to 2000 µm from a nerve canal, a separation space is planned to place the bone filler materials to maintain a distance of about 1000 µm to 2000 µm between the implant member 101 and the nerve canal. During installation of implant member 101, the unfilled area is configured to be filled with one or more flowable bone filler materials. Along the implant member 101, one or more longitudinal grooves 601 are designed to allow debris such as blood and excess bone filler material to escape from the periodontal bone socket 103a during the insertion of the dental implant 100 into the periodontal bone socket 103a. For teeth with multiple roots, the dental implant 100 is designed to ensure proper insertion into all the roots at the same time. For the unfilled undercut area that the dental implant 100 is unable to reach, bone filler graft materials can be added before the insertion of the dental implant 100.

In an embodiment, the dental implant 100, as disclosed in the detailed description of FIGS. 1A-1E, is fabricated and milled 903 according to a treatment plan formulated based on the digital simulation using a fabricator 803. In fabricating the dental implant 100, the design features and structures, for example, the shape of the implant member 101, the anchoring assembly 102, the hook-shaped micro-extensions 101h, the sandblasted micro-textured surface 402, the retentive grooves 401, the composite packing 105, other retentive and anti-rotational features, etc., that account for initial stability, long-term stability, soft tissue management, functional and esthetic requirements of the dental implant 100 are planned and/or incorporated. The implant member 101 is made from or coated with metal alloys that are bio-compatible with human tissues, for example, titanium alloys. In an embodiment, the anchoring assembly 102 comprising the first fastening element 102a and the cylindrical members 102b is machined in the center of a preformed cylinder or a block of metal alloys that constitute the implant member 101. These prefabricated cylinders or blocks can be manufactured in large numbers. Images of the implant member 101 are acquired and imported to a computer aided design (CAD)/computer aided manufacturing (CAM) milling machine 803a as exemplarily illustrated in FIG. 8. The computer aided milling machine 803a analyzes the implant member 101 and the exact position and dimensions of the pre-machined anchoring assembly 102, and is programmed to produce the fine details of the implant member 101. In an embodiment, after measuring the screw pitch of the first fastening element 102a, the apical movement of the first fastening element 102a within the implant member 101 and the corresponding radial movement of the cylindrical members 102b may also be simulated using the digital simulator 802 to predetermine the amount of anchoring force required for the implant for the patient, and in turn to predetermine the number of turns of the coronal screw head 102h of the first fastening element 102a to precisely control the anchoring force thereabout. Also, the amount of anchoring force is determined based on the type of bone of the patient and the bone density around the periodontal bone socket 103a, which can be estimated using the captured three-dimensional X-ray images data of the periodontal bone socket 103a. The second end 102g of each of the cylindrical members 102b that contacts the periodontal bone surface 103b are fabricated and milled to conform to the surface contour of the periodontal bone surface 103b, so that the second end 102g abuts against the periodontal bone surface 103b evenly as the cylindrical members 102b are radially advanced as illustrated in FIG. 10.

In an embodiment, the digital simulator 802 pre-determines 904 an anchoring force for anchoring the designed dental implant 100 to an inner wall of the periodontal bone socket 103a based on the captured three-dimensional images and implements the three-dimensional variation associated with the extraction. The natural tooth is extracted 905 using a tooth extractor and the fabricated dental implant 100 is installed into the periodontal bone socket 103a. The tooth extractor is exemplarily illustrated in the detailed description of FIG. 16. The multiple hook-shaped micro-extensions 101h integrally formed in a mid-portion 101e of a root section 101b of the fabricated dental implant 100 helps in guiding the dental implant 100 into the periodontal bone socket 103a and impede coronal movement of the inserted dental implant 100 within the periodontal bone socket 103a. The inserted dental implant 100 is anchored 906 within the periodontal bone socket 103a. The multiple radial and equidistant cylindrical members 102b disposed in the mid-portion 101e of the root section 101b of the fabricated dental implant 100 abut and evenly press against radial and equidistant cylindrical members 102b and the inner wall of the periodontal bone socket 103a which are set to attain the pre-determined anchoring force. The interstitial space 103f between the inserted dental implant 100 and the periodontal bone socket 103a is filled 907 with one or more of a bone filler material, an osteogenic material, and antibiotic agents to facilitate bone regeneration and long-term stability of the dental implant 100. The method for fabricating a dental implant 100 further comprises an implant drill 1501 for drilling an additional implant space for providing an additional anchorage in the implant member 101 within the periodontal bone socket 103a of the dental implant 100. The traditional implant drill 1501 is exemplarily illustrated in the detailed description of FIG. 15.

In an embodiment, as illustrated in FIG. 11A, the bone contacting outer surface areas 101j of the implant member 101 are engraved, sandblasted and etched with the pre-designed retentive grooves 401. The coronal surface areas 101i of the coronal section 101a of the implant member 101 that potentially contact the soft tissue are contoured to establish a tight closure with the soft tissue and smoothed and polished to avoid plaque accumulation. The coronal surface 101i of the coronal section 101a exposed to the oral cavity is coated with layers of tooth colored materials. The final product is sterilized, sealed and delivered to the dentist. With the pre-machined implant cylinders or blocks, the CAD/CAM milling machine 803a, etc., to fabricate the implant member 101, and the loading of the crown 104 onto the dental implant 100, it is possible to diagnose, design, and deliver the dental implant 100 in a single clinical appointment.

In an embodiment, the fabricated dental implant 100 is inserted into the periodontal bone socket 103a based on the established path for the insertion and the treatment plan. At the clinical appointment, local anesthetics are administered before the procedure. Prior to the insertion, atraumatic extraction techniques are used to minimize damages such as the forced expansion of the bone plates, fractures of surrounding periodontal bones 103c, and laceration of the soft tissue. 3-dimensional X-ray images can be used to plan the path of extraction to avoid undercut area and the sectioning of multiple roots that may be flared to block the path of extraction. For multi-rooted teeth, surgical procedures can be used to section the roots before the atraumatic extraction of the teeth. Infections in the periodontal bone socket 103a are removed and treated with antibiotic agents. Mixtures of bone filler materials and antibiotic agents are filled into the apical area or base 103h of the periodontal bone socket 103a. The dental implant 100 is held from the coronal section 101a to avoid contamination and inserted into the periodontal bone socket 103a at the proper orientation until the entire implant member 101 is submerged into the periodontal bone socket 103a. A post-surgical X-ray is taken to ensure the full insertion of the dental implant 100 into the periodontal bone socket 103a. The first fastening element 102a of the anchoring assembly 102 is tightened according to the digital simulation, or according to the manufacturer's recommendations. The coronal surface 101i of the coronal section 101a illustrated in FIG. 10 of the implant member 101 of the inserted dental implant 100 is filled 908 with tooth filling composite materials for the osseointegration period of the dental implant 100. If temporary crowns 104 are indicated by the dentist, the coronal surface 101i of the coronal section 101a of the implant member 101 is loaded with the temporary crowns 104 using temporary dental cement. Occlusal contacts with the dental implant 100 are verified to ensure that no occlusal contacts are strongly marked. If abnormal contacts are expected to the implanted coronal surface 101i or a crown surface, a protective guard or a splint is placed on the coronal surface 101i to avoid such contacts with the coronal section 101a of the implant member 101. The dental implant 100 may be loaded 909 with a permanent crown 104 and/or a pre-fabricated tooth colored layer at the end of the osseointegration period of the dental implant 100.

Figure 11C:
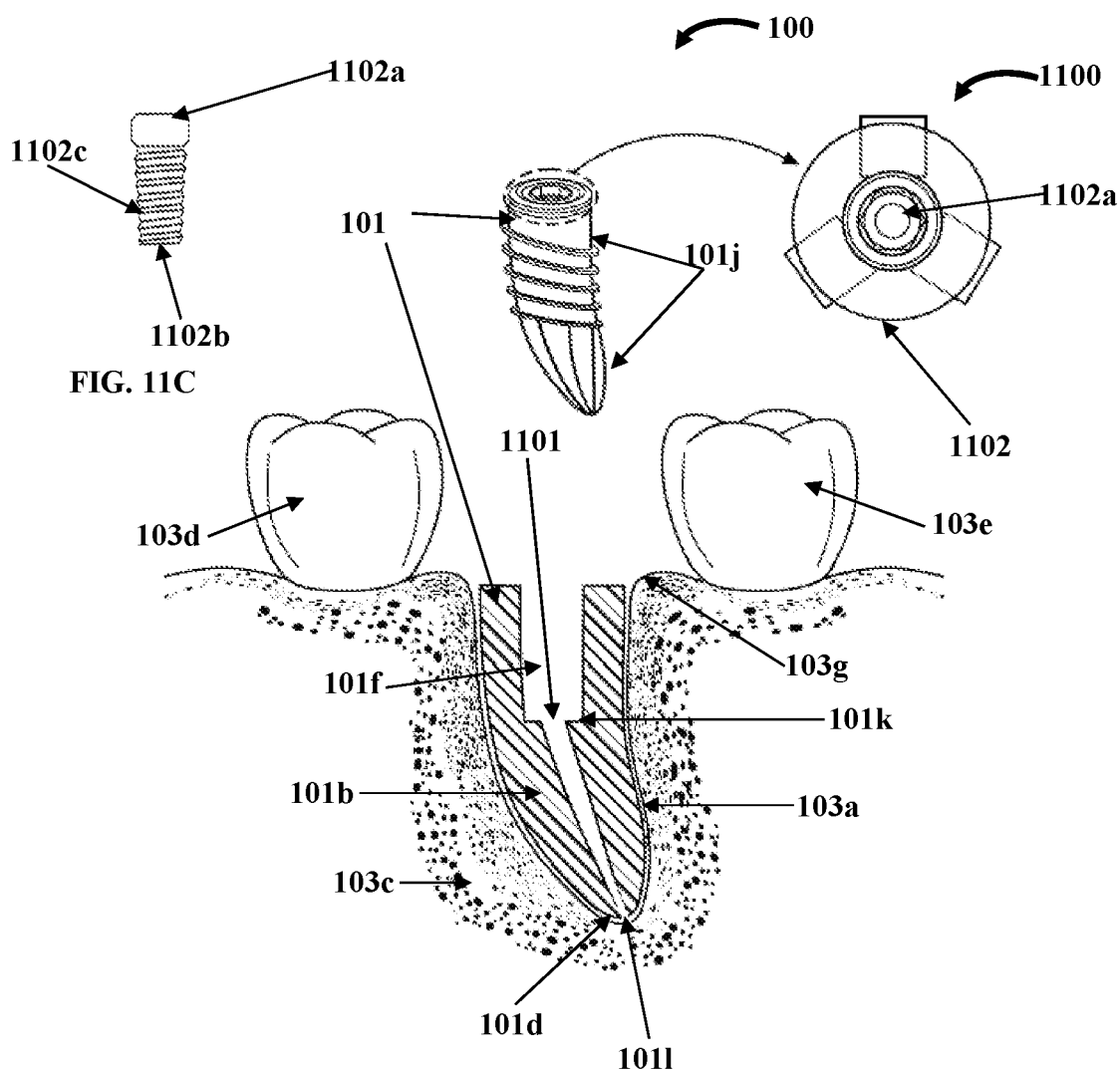
FIG. 11C exemplarily illustrates a second fastening element of the dental implant.

In an embodiment, FIG. 11A exemplarily illustrates an exploded front view of the dental implant 100 with a tapered inner canal 1101. The tapered inner canal 1101 extends from a base 101k of the hollow axial cavity 101f to the apical end 101d of the root section 101b. As used herein, "tapered inner canal" refers to a structure that is, configured to be screwably sealed with an inner canal seal 1103 exemplarily illustrated in FIG. 11B towards the apical end 101d of the root section 101b. In an embodiment, the tapered inner canal 1101 allows excess bone filler materials to escape from the surface of the periodontal bone socket 103a through the tapered inner canal 1101. The bone filler materials are, for example, an osteogenic material, antibiotic agents, etc., to ensure bone regeneration and long term stability of the dental implant 100. The tapered inner canal 1101 ensures proper delivery of antibiotic agents into the apical end 101d of the root section 101b and also avoids any possible infection from the apical end 101d of the root section 101b. The dental implant 100 further comprises a second fastening element 1102, as illustrated in FIG. 11C. The second fastening element 1102 is positioned within the tapered inner canal 1101. The second fastening element 1102 comprises a screw head 1102a, a truncated end 1102b, and a conical screw body 1102c. In an embodiment, the conical screw body 1102c of the second fastening element 1102 has a similar structure as that of the apical section 102c of the first fastening element 102a. In another embodiment, the second fastening element is similar to the first fastening element 102a, except for having a different screw head 1102a, for example, an internal hex flat-head, an internal triangular head, etc. The tapered inner canal 1101 is sealed by the screw head 1102a of the second fastening element 1102 into the apical end 101d of the root section 101b using a screw driver comprising a triangular or a hex screwdriver bit. The conical screw body 1102c of the second fastening element 1102 allows insertion of the tapered inner canal 1101 towards the apical end 101d of the root section 101b. The second fastening element 1102 is configured to screwably engage the tapered inner canal 1101 of the implant member 101, sealed with the inner canal seal 1103. The second fastening element 1102 is tightened or released within the tapered inner canal 1101 using the screw head 1102a. The second fastening element 1102 apically advances within the tapered inner canal 1101 when the second fastening element 1102 is tightened by turning the screw head 1102a. The tightening of the second fastening element 1102 allows the tapered inner canal 1101 to be extended towards the apical end 101d of the root section 101b of the implant member 101 thereby providing an opening 1011 to allow excess bone filler materials to escape through the opening. The tapered inner canal 1101 provides provision for treating possible future infections in the apical area of the implant member 101, allows draining the abscess, and provides provision for delivering medicine to the infected area. In an embodiment, the tapered inner canal 1101 is sealed to prevent contamination due to debris entering the bone socket 103a through the tapered inner canal 1101. Not shown in FIG. 11A is the first fastening element 102 for anchoring the implant member 101 of the dental implant 100 within the follow axial cavity 101f, as disclosed in the detailed description of the FIGS. 1A-1G. Also not shown in FIG. 11A are the multiple hook shaped micro-extensions 101h circumferentially disposed around the root section 101b of the implant number 101, as disclosed in the detailed description of FIGS. 1A-1G.

Figure 12:
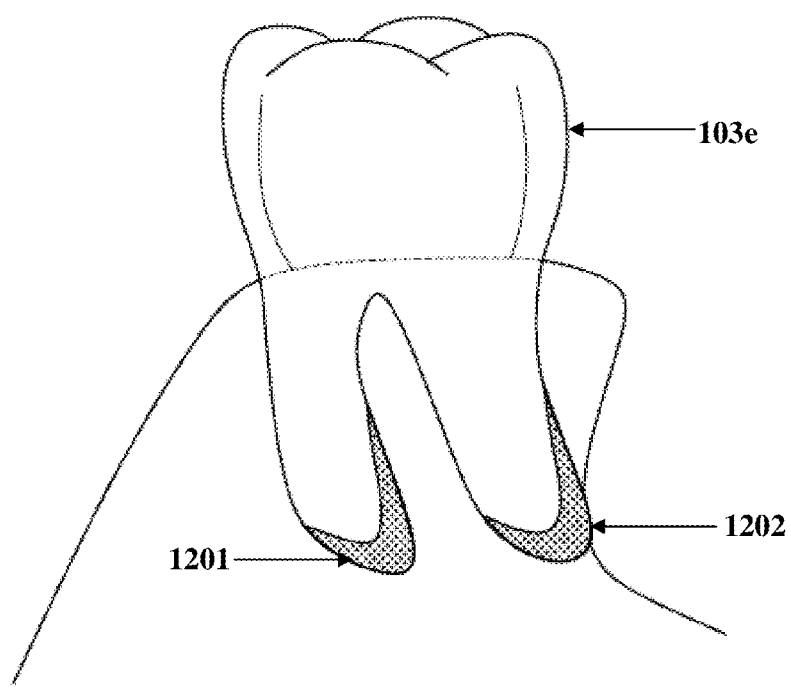
FIG. 12 exemplarily illustrates the natural tooth with undercut area and insufficient bone area.

In an embodiment, FIG. 12 exemplarily illustrates the natural tooth 103e comprising undercut area 1201 and insufficient bone area 1202. As used herein, "undercut area" refers to a portion of a natural tooth 103e that lies between its height of contour and the gingiva, only if that portion is of a lesser circumference than the height of contour. Also, as used herein, "insufficient bone area" refers to a portion of the natural tooth 103e where there is minimal bone growth. FIG. 7 discloses a method for installing the dental implant 100 comprising grooves 401 on the root section 101b of the implant member 101.

The alternate embodiment of the method for installing the dental implant 100 comprising retentive spiral grooves 1001a and 1001b diagonal to the periodontal bone socket 103a provided in the description of FIGS. 10, 11A and 11B further comprises determining one or more undercut area 1201 at a root of the natural tooth 103e, as shown in FIG. 12. The one or more undercut area 1201 prevents insertion of the dental implant 100. The determined one or more undercut areas 1201 are removed by filling the one or more undercut area 1201 using one or more bone filler material thereby allowing insertion of the dental implant 100. The bone filler material ensures bone regeneration and long term stability of the dental implant 100 as exemplarily illustrated in FIG. 1F. In an embodiment, the method to provide the dental implant 100 further comprises determining one or more insufficient bone area 1202 at the root of the natural tooth 103e before inserting the implant member 101 into the periodontal bone socket 103a. In an embodiment, the dental implant 100 is further modified by the determined insufficient bone area 1202 to allow sufficient bone growth using one or more bone filler material if the root of the natural tooth 103e does not have sufficient bone support.

Figure 13:
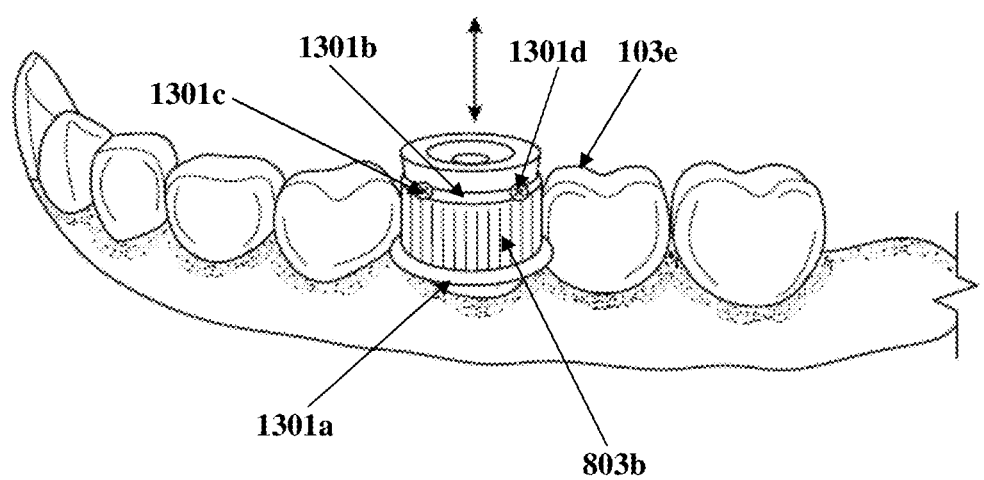
FIG. 13 exemplarily illustrates a customized surgical guide for fabricating and milling the dental implant.

In an embodiment, FIG. 13 exemplarily illustrates a customized surgical guide 803b for fabricating and milling the dental implant 100. In an embodiment, a system 800 for fabricating and installing a dental implant 100 and restoration for a patient is provided, as exemplarily illustrated in FIG. 8. The system 800 disclosed herein comprises a three-dimensional (3D) imaging device 801, a digital simulator 802, and a fabricator 803. The fabricator 803 further comprises a customized surgical guide 803b. The customized surgical guide 803b acts as an anchor to extrude the natural tooth 103e from the periodontal bone socket 103a and guides precise insertion and tapping of the dental implant 100 into the periodontal bone socket 103a along the exact path of the extracted natural tooth. The customized surgical guide 803b also acts as a protection shield from infection in the oral cavity during the insertion process of the dental implant 100.

Figure 14A:
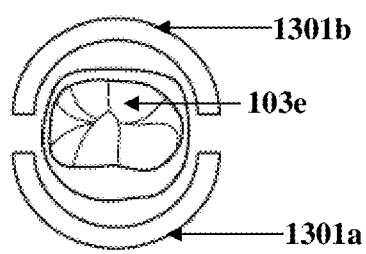
FIGS. 14A exemplarily illustrates a top view of a natural tooth and a position of a customized surgical guide on the natural tooth.
Figure 14B:
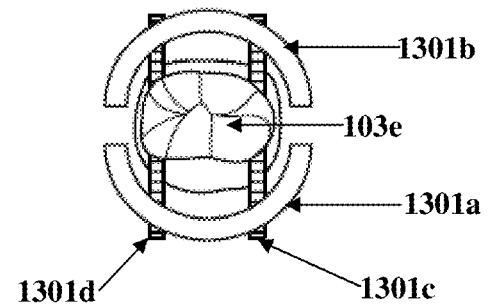
FIG. 14B exemplarily illustrates another view of the natural tooth and the position of the customized surgical guide on the natural tooth.
Figure 14C:
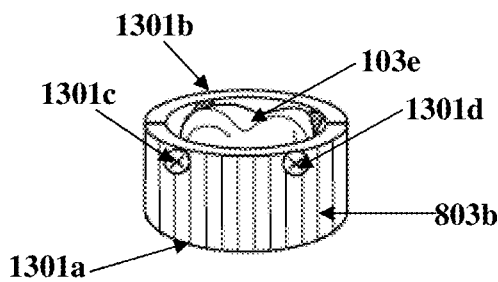
FIG 14C exemplarily illustrates another top view of the natural tooth and the position of the customized surgical guide on the natural tooth.

In an embodiment, FIGS. 14A-14C exemplarily illustrates the top view of the natural tooth 103e and the position of the customized surgical guide 803b on the natural tooth 103e. The customized surgical guide 803b as exemplarily illustrated in FIG. 13 comprises an inner ring 1301a and an outer ring 1301b. The inner ring 1301a and outer ring 1301b are, for example, custom shaped to brace the natural tooth 103e from the inner surface and outer surface of the natural tooth 103e as exemplarily illustrated in FIG. 14A. The inner ring 1301a and outer ring 1301b are fastened using a first tightening screw 1301c and a second tightening screw 1301d as exemplarily illustrated in FIG. 14B. The first tightening screw 1301c and the second tightening screw 1301d are placed perpendicular to the inner ring 1301a and the outer ring 1301b of the customized surgical guide 803b. In an embodiment, the inner ring 1301a and the outer ring 1301b are embedded inside the customized surgical guide 803b. The embedded inner ring 1301a and outer ring 1301b are then inserted over the natural tooth 103e then tightened by the first tightening screw 1301c and the second tightening screw 1301d as exemplarily illustrated in FIG. 14C. The top of the outer ring 1301b is opened from the customized surgical guide 803b so that the opened outer ring 1301b can be lifted up for extracting the natural tooth 103e from the periodontal bone socket 103a. After the extraction of the natural tooth 103e, the dental implant 100 is inserted into the periodontal bone socket 103a along the exact path of the extracted natural tooth 103e by tapping the implant member 101 along the path of insertion into the periodontal bone socket 103a through precision guided incremental steps. The customized surgical guide 803b indicates the three dimensional orientation of the insertion of the implant member 101. The precision guided incremental steps comprises, attaching the customized surgical guide 803b to the implant member 101 using a guide screw shaped first fastening element 102a, the implant member 101 attached to the customized surgical guide 803b is precisely oriented to the periodontal bone socket 103a until the insertion is stopped by contact with the periodontal bone socket 103a. The implant member 101b is further inserted into the periodontal bone socket 103a by applying a gentle repetitive tapping force along the path of insertion over the top of the customized surgical guide 803b until the customized surgical guide 803b indicates that the implant member 101 is fully inserted into the periodontal bone socket 103a. Thereafter the customized surgical guide 803b is detached from the implant member 101 by unscrewing the guide screw shaped first fastening element 102a.

Figure 15:
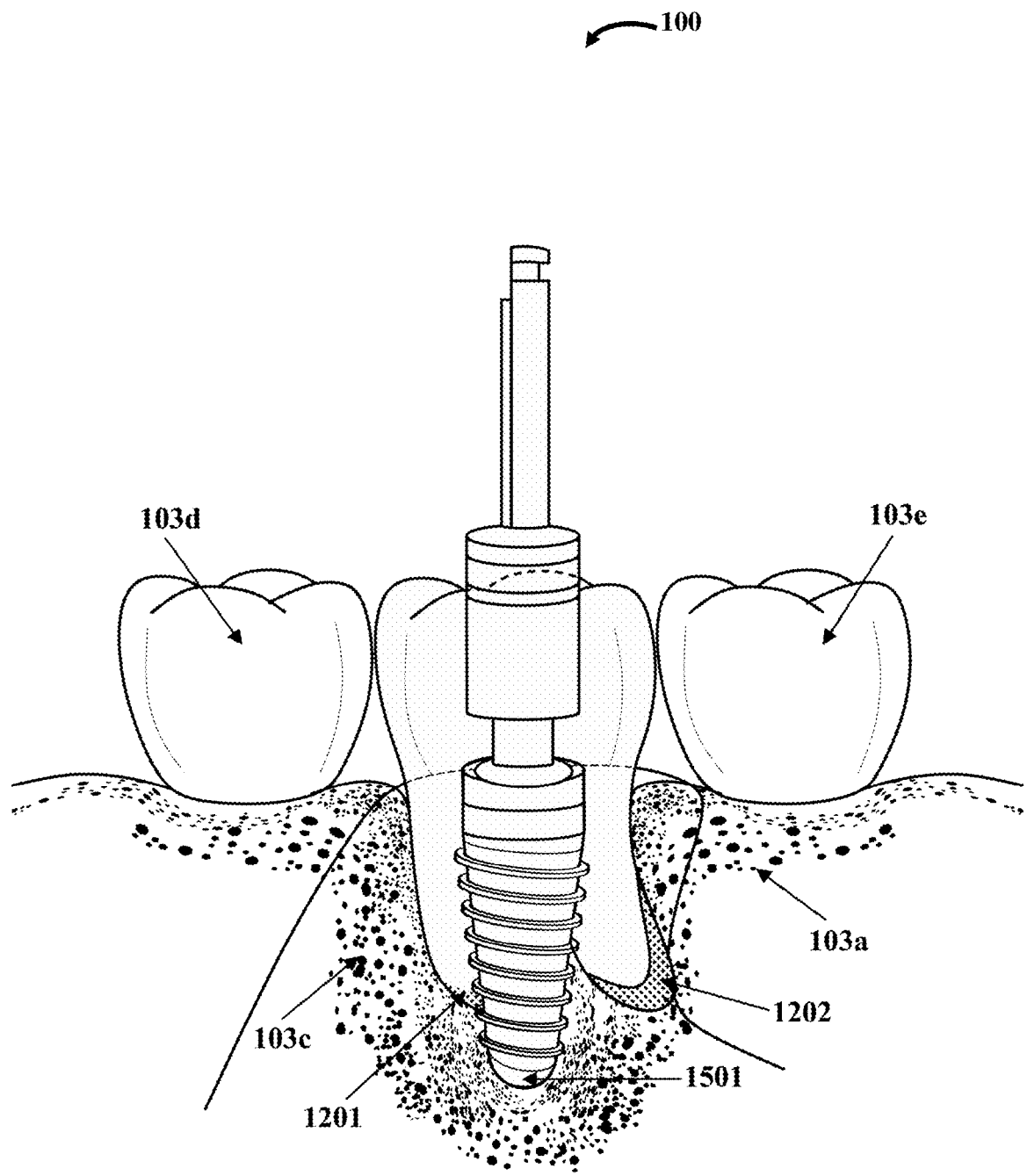
FIG. 15 exemplarily illustrates a perspective view of the dental implant with a traditional implant drill.

In an embodiment, FIG. 15 exemplarily illustrates a perspective view of the dental implant 100 with a traditional implant drill 1501. The method for providing the dental implant 100 is exemplarily illustrated in the detailed description of FIG. 7. The method for providing the dental implant 100 further comprises a traditional implant drill 1501 for drilling an additional implant space. The traditional implant drill 1501 provides an additional anchorage in the implant member 101 within the periodontal bone socket 103a of the dental implant 100. The direction and the depth of the additional implant space is determined by using a precision custom guide. The determined depth of the implant space is further incorporated in the implant member 101 using the implant drill 1501 thereby providing the additional anchorage in the implant member 101 within the periodontal bone socket 103a of the dental implant 100. In general, the implant member 101 is for example, titanium oxide since the implant member 101 is exposed in the oral cavity. In an embodiment, the implant member 101 is made of zirconium because of the biocompatible properties of zirconium oxide. For example, the digital simulator 802 shown in FIG. 8 indicates that an additional anchorage is required with the traditional implant drill 1501. The traditional implant drill is, for example, an implant drill manufactured by Noble Biocare of Kloten, Switzerland with a diameter of about 3 mm and a length of about 8 mm. A customized surgical guide 803b shown in FIG. 13 is used to precisely guide the orientation and depth of the traditional implant drill 1501. A traditional implant motor is used to drill the traditional implant drill 1501 into the periodontal bone socket 103a. The implant member 101 acquires stronger anchorage with the drilled periodontal bone socket 103a comprising the socket for both natural tooth 103e and the traditional implant drill 1501.

Figure 16:
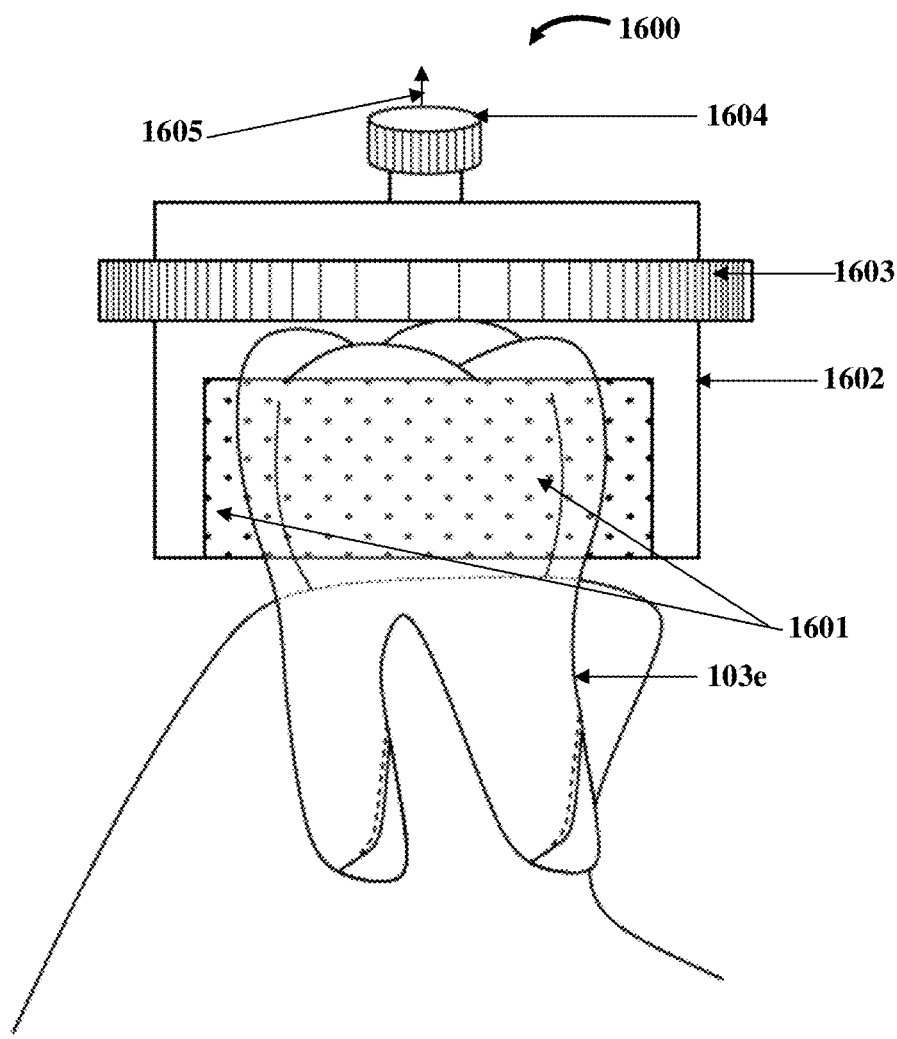
FIG. 16 exemplarily illustrates a tooth extractor for extracting the natural tooth.

In an embodiment, FIG. 16 exemplarily illustrates a tooth extractor 1600 for extracting the natural tooth 103e. The tooth extractor 1600 for extracting the natural tooth 103e comprises multiple facial and lingual bracing parts 1601, a lift button 1604, and a vibrational force transducer 1605. As used herein, "tooth extractor" refers to a device to extract the natural tooth 103e without damaging the bone structure. The natural tooth 103e can be extracted using the captured three-dimensional images of the natural tooth 103e and the three-dimensional image of the bone that is proximal to the natural tooth 103e to be extracted. The facial and lingual bracing parts 1601 are positioned on the natural tooth 103e to be extracted thereby firmly holding the coronal portion 101a of the natural tooth 103e with a metal ring 1602 and tightened using a tightening screw 1603. The facial and lingual bracing parts 1601 are for example, custom built to meet the patient's requirements. The lift button 1604 is positioned on top of the metal ring 1602 connecting to a lever 1701 for providing a strong lifting force in a direction coronal to extract the natural tooth 103e along the path of eruption determined by one or more three dimensional images of the root of the natural tooth 103e as exemplarily illustrated in FIG. 17. The vibrational force transducer 1605 is positioned on top of the lift button 1604 thereby loosening the periodontal ligament before the extraction of the natural tooth 103e. The vibrational force transducer 1605 taps the implant member 101 along the path of insertion into the periodontal bone socket 103a through precision guided incremental steps as exemplarily illustrated in the detailed description of FIG. 15.

Figure 17:
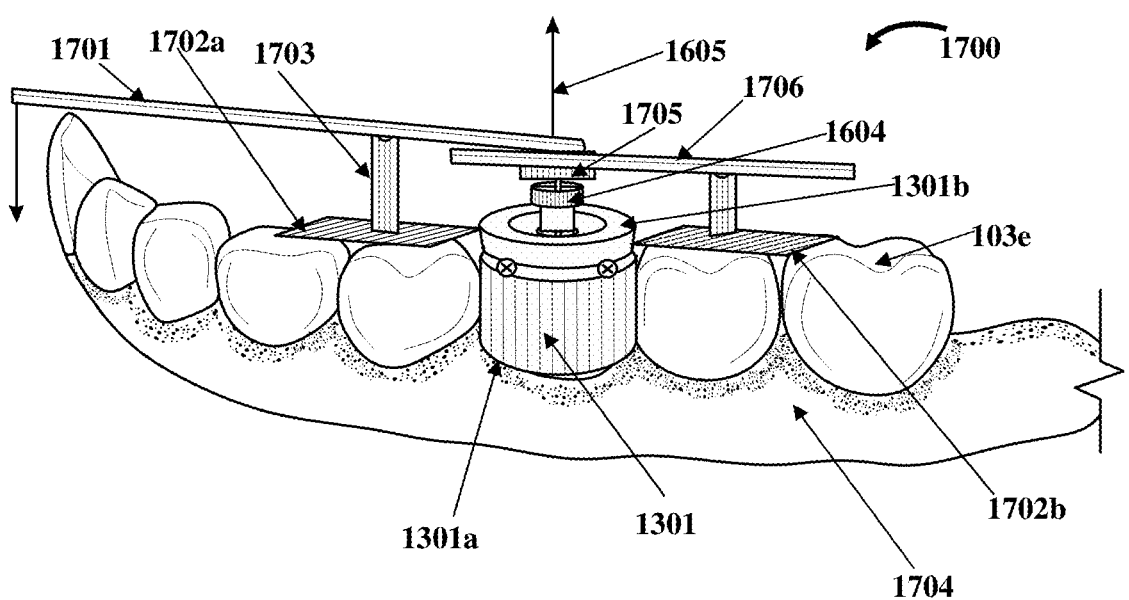
FIG. 17 exemplarily illustrates a system for extracting the natural tooth.

In an embodiment, FIG. 17 exemplarily illustrates a system 1700 for extracting the natural tooth 103e. The system 1700 for extracting the natural tooth 103e comprises a custom tray 1704, a lever arm 1701, a pivot support 1703, one or more support plates 1702a and 1702b, a button engager 1705, and a tooth extractor 1600 for extracting the natural tooth 103e exemplarily illustrated in the detailed description of FIG. 16. The support plates 1702*a* and 1702*b* are positioned on the natural tooth 103*e* surface and the support plates 1702*a* and 1702*b* is in proximal connectivity to the lever arm 1701 and the pivot support 1703. The support plates 1702*a* and 1702*b*, for example, is a rectangle table placed over both sides of the natural tooth 103*e* connected through a metal bar 1706 over the surface surrounding the natural tooth 103*e*. The diameter of the button engager 1705 is wider than the diameter of the lift button 1604 and engaged securely into the undercut area of the lift button 1604 from the sides of the natural tooth 103*e*. A displacement of 1-2 mm is provided to lift the natural tooth 103*e* off the periodontal bone socket 103*a*. Hence, a gentle elevation is provided to loosen the periodontal ligament before the extraction of the natural tooth 103*e* using the vibrational force transducer 1605. The lever arm 1701 firmly secured to the lift button 1604 and hinged over the pivot support 1703 mounted to the support plates 1702*a* and 1702*b* delivers the lifting force by lifting the natural tooth 103*e* in a direction perpendicular over the button engager 1705.

In an embodiment, FIG. 18 exemplarily illustrates a two-dimensional periapical image taken at different angles of the natural tooth 103*e*. A system 800 for fabricating the dental implant 100 is exemplarily illustrated in the detailed description of FIG. 8. High-resolution three-dimensional image of the natural tooth 103*e* are required to precisely and securely place the dental implant 100 in the periodontal bone socket 103*a*. The resolution of the captured three-dimensional images from the cone beam X-ray is limited in Digital Imaging and Communications in Medicine (DICOM). The captured high-resolution three-dimensional images of the natural tooth 103*e* is further enhanced using a two-dimensional periapical X-ray image by overlapping the captured high-resolution three-dimensional images with the two-dimensional periapical X-ray image of the natural tooth 103*e*. The resolution of an ideal periapical image is, for example 20 μm whereas the resolution of three-dimensional image obtained from a cone beam X-ray is, for example, 200 μm. The periapical image is captured using a solid digital sensor without any distortion from bending the image plate.

In an embodiment, the two-dimensional periapical images are captured at multiple angles at the natural tooth 103*e*. The unstructured three-dimensional images obtained from DICOM is rotated in all the three dimensions in order to obtain the most overlap with the outline of the two-dimensional periapical images. The captured three-dimensional DICOM images are aligned at right angle and oriented with the two-dimensional periapical images. The outline of precise two-dimensional periapical images is used to correct the unstructured three-dimensional DICOM images. This process is repeated at different angles until the resolution of the captured three-dimensional images of the natural tooth 103*e* is not improved any further.

Figure 20:
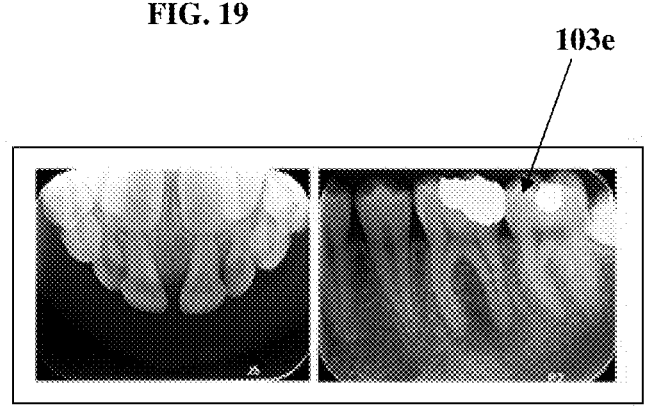
FIG. 20 exemplarily illustrates a two-dimensional peri-apical image of the natural tooth for refining the existing three-dimensional image of the natural tooth.

In an embodiment, FIG. 20 exemplarily illustrates a two-dimensional periapical image of the natural tooth 103*e* for refining the existing three-dimensional image of the natural tooth 103*e*. The two-dimensional periapical X-ray image is further configured for converting a density function of the captured one or more three dimensional images to a density function of the two-dimensional periapical X-ray images thereby improving the resolution of the captured three-dimensional images of the natural tooth 103*e*. The two-dimensional periapical images also provide a gradient of the natural tooth 103*e* and the outline of the natural tooth 103*e*. As used herein, "gradient" refers to a shadow of the natural tooth 103*e*. The captured three-dimensional DICOM images are converted into the density function that matches the gradient of the two-dimensional periapical image since the density of the root of the natural tooth 103*e* are distributed symmetrically along the axis of the root of the natural tooth 103*e*. This process along with the outline of the structure of the natural tooth 103*e* in the two-dimensional periapical images combined improves the resolution of the three-dimensional DICOM image. In an embodiment, the image data for the three-dimensional DICOM image is reduced by parametrically characterizing the root of the natural tooth 103*e* since they are symmetrical around its axis and regularly shaped. The root outline of the natural tooth 103*e* is parametrized, for example, as a series of exponential functions as exemplarily illustrated in FIG. 19 for parameterizing the root of the natural tooth 103*e*. The parameters of the root are refined by matching the two-dimensional periapical images to a higher resolution using less parametrical data.

Figure 21A:
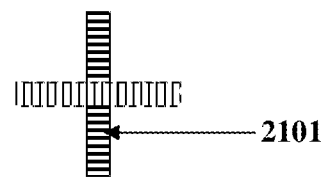
FIGS. 21A exemplarily illustrates a metal plate and its position for calibrating a density of a three-dimensional image of a natural tooth.
Figure 21B:
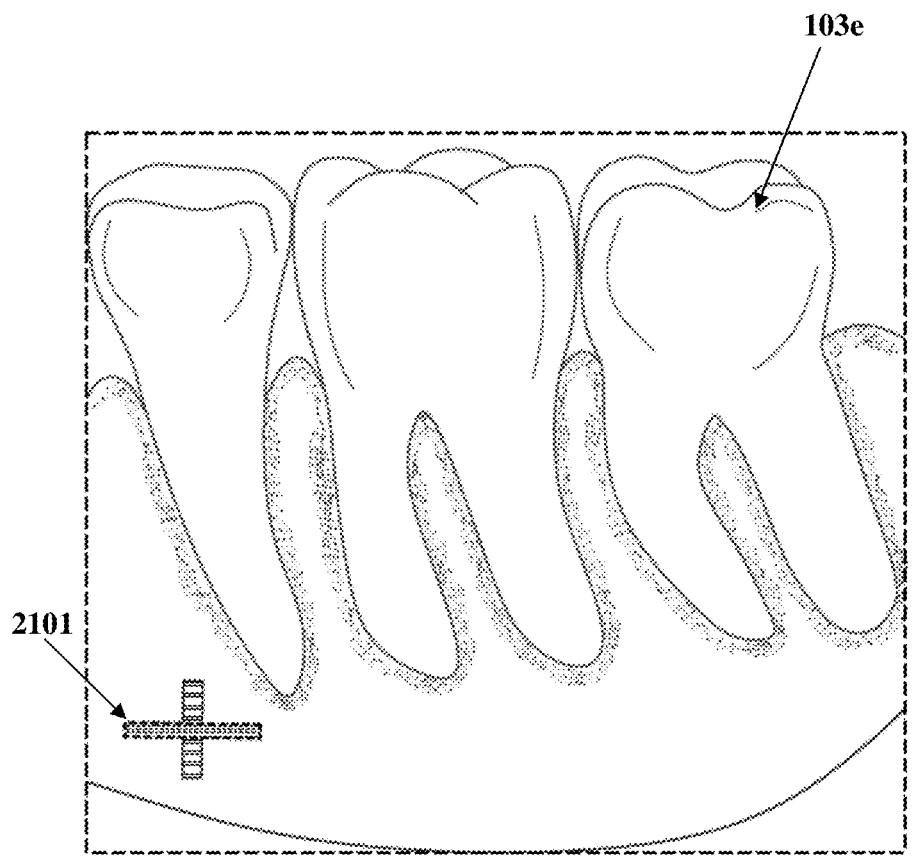
FIG 21B exemplarily illustrates the metal plate of FIG. 21A positioned proximal to a border of an X-ray detector.

In an embodiment, FIGS. 21A-21B exemplarily illustrates a metal plate 2101 and its position for calibrating the density of the three-dimensional images of the natural tooth 103*e*. In an embodiment, the metal plate 2101 is positioned proximal to the natural tooth 103*e*. In another embodiment, the metal plate is positioned proximal to a border of an X-ray detector, for example, an image plate, a flat panel detector, etc., as shown in FIG. 21B. As exemplarily illustrated in FIG. 21A, metal plates and frames 2101 are used to calibrate the density of the three-dimensional X-ray image. Metal plates and frames 2101 also coordinate the orientation of the natural tooth 103*e* in the two-dimensional periapical images and three-dimensional DICOM images. In an embodiment, the visible coronal portion of the natural tooth 103*e* are scanned using an intra oral scanner where the light of the scanner is limited to reaching the space between the natural tooth 103*e*. The three-dimensional images obtained from the scanner is of low resolution and are used for the successful restoration of the dental implant 100. The two-dimensional periapical images are used to refine the existing three-dimensional images obtained from the intra oral scanner. The metal plates and frames provide graded thickness of metal with different levels of grayness in the X-ray. The levels of grayness are then compared to the density of the natural tooth 103*e* and the bone. The levels of grayness are used to determine the quantity of the bone density and the natural tooth 103*e* in the formation of the density function of the natural tooth 103*e*.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A dental implant, comprising:
   an implant member for insertion into a periodontal bone socket of an extracted natural tooth, said implant member comprising a coronal section and a root section having a coronal end and an apical end, said coronal section axially extending from said coronal end of said root section;

an anchoring assembly positioned within a hollow axial cavity of said implant member, wherein said anchoring assembly anchors said implant member within said periodontal bone socket, said anchoring assembly comprising:

a first fastening element engaged with said implant member, said first fastening element positioned within said hollow axial cavity, wherein said first fastening element comprises an apical section having a conical shaft and a truncated end, wherein said first fastening element is threaded to screwably engage said hollow axial cavity of said implant member, wherein said first fastening element further comprises a coronal screw head for one of tightening and releasing said first fastening element within said hollow axial cavity, and wherein said first fastening element apically advances within said hollow axial cavity when said first fastening element is tightened by turning said coronal screw head; and one or more radial and equidistant cylindrical members positioned proximal to said root section, wherein said root section of said implant member comprises one or more through-holes for radially and forcibly sliding said one or more radial and equidistant cylindrical members through said one or more through-holes, wherein each of said one or more radial and equidistant cylindrical members comprises a first end that interfaces with said conical shaft of said first fastening element, and a second end that interfaces against a surface of said periodontal bone socket;

said implant member further comprising a tapered inner canal extending from a base of said hollow axial cavity to said apical end of said root section; and a second fastening element positioned within said tapered inner canal, wherein said second fastening element comprises a screw head, a truncated end, and a conical screw body, said second fastening element is configured to screwably engage said tapered inner canal of said implant member, wherein said second fastening element is one of tightened and released within said tapered inner canal, wherein said second fastening element apically advances within said tapered inner canal when said second fastening element is tightened by turning said screw head of said second fastening element, and wherein said second fastening element apically retracts within said tapered inner canal when said second fastening element is released by turning said screw head of said second fastening element.

2. The dental implant of claim 1, wherein said conical shaft of said first fastening element radially and outwardly pushes said one or more radial and equidistant cylindrical members through said through-holes when said first fastening element is apically advanced within said hollow axial cavity, whereby said second end of each of said one or more radial and equidistant cylindrical members presses substantially uniformly against said surface of said periodontal bone socket to generate an anchoring force to anchor said implant member within said periodontal bone socket.

3. The dental implant of claim 2, wherein said first fastening element enables a dentist to control said anchoring force generated by said one or more radial and equidistant cylindrical members using said coronal screw head of said first fastening element.

4. The dental implant of claim 1, wherein said implant member further comprises a plurality of hook shaped extensions fabricated to point upwards towards said coronal section of said implant member circumferentially disposed around said root section of said implant member, wherein said hook shaped extensions anchor said surface of said periodontal bone socket for impeding coronal movement of said inserted implant member within said periodontal bone socket.

5. The dental implant of claim 1, wherein said implant member further comprises one or more longitudinal grooves parallel to said periodontal bone socket or one or more spiral grooves diagonal to said periodontal bone socket for allowing debris to escape out of said periodontal bone socket during said insertion of said implant member within said periodontal bone socket.

6. The dental implant of claim 1, wherein said implant member further comprises an outer surface, wherein said outer surface is a sandblasted micro-textured surface, wherein said outer surface comprises retentive grooves along a mid-portion of said root section of said implant member to increase contact area between said implant member and said surface of said periodontal bone socket.

7. The dental implant of claim 1, further comprising a composite packing disposed on a coronal surface of said coronal section of said implant member, wherein said composite packing is filled with tooth filling composite materials, wherein said composite packing avoids direct contact of said implant member with opposing teeth to reduce parafunctional interferences during an osseointegration period.

8. The dental implant of claim 1, wherein said surface of said periodontal bone socket and an outer surface of said implant member define an interstitial space therebetween after said insertion of said implant member within said periodontal bone socket, wherein said interstitial space is filled with one or more of a bone filler material, an osteogenic material, and antibiotic agents to ensure bone regeneration and long term stability of said dental implant.

9. The dental implant of claim 1, wherein said inserted dental implant is loaded with one or more of a permanent crown and a pre-fabricated tooth colored layer after an osseointegration period.

10. The dental implant of claim 1, wherein said tapered inner canal is further configured for allowing excess one or more bone filler materials to escape from said surface of said periodontal bone socket through said tapered inner canal.

11. A method for installing a dental implant, comprising:
providing said dental implant comprising:
an implant member for insertion into a periodontal bone socket of an extracted natural tooth, said implant member comprising a coronal section and a root section having a coronal end and an apical end, said coronal section axially extending from said coronal end of said root section;

an anchoring assembly positioned within a hollow axial cavity of said implant member, wherein said anchoring assembly anchors said implant member within said periodontal bone socket, said anchoring assembly comprising:

a first fastening element engaged with said implant member, said first fastening element positioned within said hollow axial cavity, wherein said first fastening element comprises an apical section having a conical shaft and a truncated end, wherein first said fastening element is threaded to screwably engage said hollow axial cavity of said implant member, wherein said first fastening element comprises a coronal screw head for one of tightening and releasing said first fastening element within said hollow axial cavity, wherein said first fastening element is apically advanced within said hollow axial cavity when said first fastening element is tightened by turning said coronal screw head; and one or more radial and equidistant cylindrical members positioned proximal to said root section, wherein said root section of said implant member comprises one or more through-holes for radially and forcibly sliding said one or more radial and equidistant cylindrical members through said one or more through-holes, wherein each of said one or more radial and equidistant cylindrical members comprises a first end that interfaces with said conical shaft of said first fastening element, and a second end that interfaces against a surface of said periodontal bone socket; and said implant member further comprising a tapered inner canal extending from a base of said hollow axial cavity to said apical end of said root section; and a second fastening element as part of said anchoring assembly, wherein said second fastening element is positioned within said tapered inner canal, wherein said second fastening element comprises a screw head, a truncated end, and a conical screw body, said second fastening element is configured to screwably engage said tapered inner canal of said implant member;

inserting said implant member with said anchoring assembly of said dental implant into said periodontal bone socket;

apically advancing said first fastening element of said anchoring assembly within said hollow axial cavity, whereby said conical shaft of said first fastening element radially and outwardly pushes said one or more radial and equidistant cylindrical members through said through-holes and presses said second end of each of said one or more radial and equidistant cylindrical members substantially uniformly against said surface of said periodontal bone socket to generate an anchoring force to anchor said implant member within said periodontal bone socket; and one of tightening or releasing said second fastening element within said tapered inner canal, wherein said second fastening element apically advances within said tapered inner canal when said second fastening element is tightened by turning said screw head of said second fastening element, and wherein said second fastening element apically retracts within said tapered inner canal when said second fastening element is released by turning said screw head of said second fastening element.

12. The method of claim 11, further comprising filling an interstitial space defined between said surface of said periodontal bone socket and said outer surface of said implant member, after said insertion of said implant member within said periodontal bone socket, with one or more of a bone filler material, an osteogenic material, and antibiotic agents to ensure bone regeneration and long term stability of said dental implant.

13. The method of claim 11, wherein providing said dental implant further comprises:

determining one or more undercut area at a root of said natural tooth that prevents insertion of said dental implant and variation of said periodontal bone socket space due to an extraction force;

removing said determined one or more undercut area by filling said one or more undercut area using one or more bone filler material thereby allowing insertion of said dental implant.

14. The method of claim 11, further comprising determining one or more insufficient bone area at said root of said natural tooth before inserting said implant member into said periodontal bone socket, and modifying said dental implant to allow sufficient bone growth using said one or more bone filler material if said root of said natural tooth does not have sufficient bone support.

15. The method of claim 11, further comprising providing a plurality of hook shaped extensions bent upwards towards said coronal section of said implant member circumferentially around said root section of said implant member, wherein said hook shaped extensions anchor said surface of said periodontal bone socket for impeding coronal movement of said inserted implant member within said periodontal bone socket.

16. The method of claim 11, further comprising providing one of:

one or more longitudinal grooves on said implant member parallel to said periodontal bone socket; and one or more spiral grooves diagonal to said periodontal bone socket for allowing debris to escape from said periodontal bone socket during said insertion of said implant member into said periodontal bone socket.

17. The method of claim 11, further comprising controlling an anchoring force generated by said one or more radial and equidistant cylindrical members using said coronal screw head of said first fastening element by a dentist.

18. The method of claim 11, further comprising sandblasting an outer surface of said implant member to obtain a sandblasted micro-textured surface and providing retentive grooves on said outer surface of said implant member along said mid-portion of said root section of said implant member to increase contact area between said implant member and said surface of said periodontal bone socket.

19. The method of claim 11, further comprising providing a composite packing on a coronal surface of said implant member, wherein said composite packing is filled with tooth filling composite materials, wherein said composite packing avoids direct contact of said implant member with opposing teeth to reduce para-functional interferences during an osseointegration period.

20. The method of claim 11, further comprising drilling an implant space using a traditional implant drill for providing an additional anchorage in said implant member within said periodontal bone socket of said dental implant, wherein said drilling is performed prior to said insertion of said implant member into said periodontal bone socket.

21. The method of claim 11, further comprising loading said inserted dental implant with one or more of a permanent crown and a pre-fabricated tooth colored layer after an osseointegration period.

* * * * *